(12) United States Patent
Baran et al.

(10) Patent No.: US 7,914,517 B2
(45) Date of Patent: Mar. 29, 2011

(54) SYSTEM AND METHOD FOR MANIPULATING A CATHETER FOR DELIVERING A SUBSTANCE TO A BODY CAVITY

(75) Inventors: George Baran, London (CA); J. Michael Nuttall, London (CA)

(73) Assignee: Trudell Medical International, London, Ontario (CA)

( * ) Notice: Subject to any disclaimer, the term of this patent is extended or adjusted under 35 U.S.C. 154(b) by 1084 days.

(21) Appl. No.: 10/978,692

(22) Filed: Nov. 1, 2004

(65) Prior Publication Data
US 2005/0125002 A1    Jun. 9, 2005

Related U.S. Application Data

(60) Provisional application No. 60/516,258, filed on Oct. 31, 2003.

(51) Int. Cl.
*A61M 25/00*    (2006.01)
(52) U.S. Cl. ...................................................... 604/528
(58) Field of Classification Search ................ 604/108, 604/158, 164.01, 528, 530
See application file for complete search history.

(56) References Cited

U.S. PATENT DOCUMENTS

| | | |
|---|---|---|
| 442,785 A | 12/1890 | Schoettl |
| 606,240 A | 6/1898 | Prescott |
| 790,318 A | 5/1905 | Sams |
| 817,819 A | 4/1906 | Walkup |
| 829,952 A | 9/1906 | Dean |
| 852,154 A | 4/1907 | Bariffi |
| 970,576 A | 9/1910 | Trautmann |
| 1,786,394 A | 12/1930 | Tracy |
| 1,990,824 A | 2/1935 | Gustafsson |
| 2,019,941 A | 11/1935 | Tracy |
| 2,029,423 A | 2/1936 | Gustafsson |
| 2,070,695 A | 2/1937 | Tracy |
| 2,070,696 A | 2/1937 | Tracy |
| 2,204,599 A | 6/1940 | Jenkins |
| 2,235,708 A | 3/1941 | Jenkins |
| 2,271,779 A | 2/1942 | Peeps |

(Continued)

FOREIGN PATENT DOCUMENTS

EP    0 369 764 B1    6/1994

(Continued)

OTHER PUBLICATIONS

International Search Report for Application No. PCT/IB2004/003566 dated Mar. 21, 2005.

(Continued)

*Primary Examiner* — Nicholas D Lucchesi
*Assistant Examiner* — Aarti B Berdichevsky
(74) *Attorney, Agent, or Firm* — Brinks Hofer Gilson & Lione

(57) ABSTRACT

A system and method for adjusting a catheter to create a medicated atmosphere in an organ, or body cavity is disclosed. The system comprises a catheter, such as an aerosolization catheter, that can be manipulated during use and an introduction device for the introduction and manipulation, by rotational and/or axial positioning, of the aerosolization catheter. The method includes inserting the catheter into a body cavity via an introducer apparatus and adjusting an angle or orientation of the exit end of the catheter so that a substance provided to the catheter will be controllably applied to the body cavity at desired locations.

9 Claims, 17 Drawing Sheets

U.S. PATENT DOCUMENTS

| | | | |
|---|---|---|---|
| 2,633,908 A | 4/1953 | Brierly | |
| 2,646,314 A | 7/1953 | Peeps | |
| 2,722,935 A | 11/1955 | Thompson et al. | |
| 2,814,530 A | 11/1957 | Portillo | |
| 2,857,915 A | 10/1958 | Sheridan | |
| 2,942,790 A | 6/1960 | Starkey et al. | |
| 3,269,389 A | 8/1966 | Meurer et al. | |
| 3,306,289 A | 2/1967 | Cameto et al. | |
| 3,370,112 A | 2/1968 | Pierre | |
| 3,464,434 A | 9/1969 | Nielsen | |
| 3,484,044 A | 12/1969 | Dombruch et al. | |
| 3,561,444 A | 2/1971 | Boucher | |
| 3,634,924 A | 1/1972 | Blake et al. | |
| 3,762,409 A | 10/1973 | Lester | |
| 3,812,854 A | 5/1974 | Michaels et al. | |
| 3,853,105 A | 12/1974 | Kenagy | |
| 3,862,907 A | 1/1975 | Shimotsuma et al. | |
| 3,982,533 A | 9/1976 | Wiest | |
| 4,048,992 A | 9/1977 | Lindemann et al. | |
| 4,109,656 A | 8/1978 | Goethel et al. | |
| 4,207,887 A | 6/1980 | Hiltebrandt et al. | |
| 4,245,979 A | 1/1981 | Ito | |
| 4,265,237 A | 5/1981 | Schwanbom et al. | |
| 4,270,530 A | 6/1981 | Baum et al. | |
| 4,273,293 A | 6/1981 | Hastings | |
| 4,319,155 A | 3/1982 | Nakai et al. | |
| 4,327,721 A | 5/1982 | Goldin et al. | |
| 4,464,169 A | 8/1984 | Semm | |
| 4,488,548 A | 12/1984 | Agdanowski | |
| 4,495,946 A | 1/1985 | Lemer | |
| 4,502,482 A | 3/1985 | DeLuccia et al. | |
| 4,519,388 A | 5/1985 | Schwanborm et al. | |
| 4,520,812 A | 6/1985 | Freitag et al. | |
| 4,567,882 A | 2/1986 | Heller | |
| 4,580,371 A | 4/1986 | Akhavi | |
| 4,584,998 A | 4/1986 | McGrail | |
| 4,622,968 A | 11/1986 | Persson | |
| 4,632,108 A | 12/1986 | Geil | |
| 4,640,260 A | 2/1987 | Perez | |
| 4,646,733 A | 3/1987 | Stroh et al. | |
| 4,655,746 A | 4/1987 | Daniels et al. | |
| 4,661,110 A | 4/1987 | Fortier et al. | |
| 4,662,404 A | 5/1987 | LeVeen et al. | |
| 4,669,463 A | 6/1987 | McConnell | |
| 4,676,774 A | 6/1987 | Semm et al. | |
| 4,681,100 A | 7/1987 | Brychta et al. | |
| 4,690,138 A | 9/1987 | Heyden | |
| 4,691,900 A | 9/1987 | Maeda | |
| 4,699,173 A | 10/1987 | Röhling | |
| 4,735,620 A | 4/1988 | Ruiz | |
| 4,739,756 A | 4/1988 | Horn | |
| 4,805,609 A | 2/1989 | Roberts et al. | |
| 4,819,664 A | 4/1989 | Nazari | |
| 4,821,714 A | 4/1989 | Smelser | |
| 4,829,996 A | 5/1989 | Noakes et al. | |
| 4,832,012 A | 5/1989 | Raabe et al. | |
| 4,840,172 A | 6/1989 | Augustine et al. | |
| D303,840 S | 10/1989 | Weilbacher | |
| 4,878,894 A | 11/1989 | Sutter, Jr. et al. | |
| 4,881,542 A | 11/1989 | Schmidt et al. | |
| 4,884,565 A | 12/1989 | Cocozza | |
| 4,886,055 A | 12/1989 | Hoppough | |
| 4,905,497 A | 3/1990 | Shindo et al. | |
| 4,945,929 A | 8/1990 | Egilmex | |
| 4,955,375 A | 9/1990 | Martinez | |
| 4,960,134 A * | 10/1990 | Webster, Jr. | 607/116 |
| 4,976,261 A | 12/1990 | Gluck et al. | |
| 4,977,776 A | 12/1990 | Shindo et al. | |
| 4,990,133 A | 2/1991 | Solazzo | |
| 5,006,109 A | 4/1991 | Douglas et al. | |
| 5,012,804 A | 5/1991 | Foley et al. | |
| 5,025,806 A | 6/1991 | Palmer et al. | |
| 5,029,580 A | 7/1991 | Radford et al. | |
| 5,031,613 A | 7/1991 | Smith et al. | |
| 5,049,137 A | 9/1991 | Thompson | |
| 5,054,423 A | 10/1991 | Escobal | |
| 5,060,646 A | 10/1991 | Page | |
| 5,061,239 A | 10/1991 | Shiels | |
| 5,062,423 A | 11/1991 | Matson et al. | |
| 5,072,726 A | 12/1991 | Mazloomdoost et al. | |
| 5,078,131 A | 1/1992 | Foley | |
| 5,115,971 A | 5/1992 | Greenspan et al. | |
| 5,116,088 A | 5/1992 | Bird | |
| 5,119,807 A | 6/1992 | Roberts | |
| 5,121,700 A | 6/1992 | Blackwell et al. | |
| 5,125,893 A | 6/1992 | Dryden | |
| 5,143,062 A | 9/1992 | Peckham | |
| 5,146,916 A | 9/1992 | Catalani | |
| 5,152,277 A | 10/1992 | Honda et al. | |
| 5,152,745 A | 10/1992 | Steiner et al. | |
| 5,158,536 A | 10/1992 | Sekins et al. | |
| 5,167,622 A | 12/1992 | Muto | |
| 5,178,138 A | 1/1993 | Walstrom et al. | |
| 5,186,166 A | 2/1993 | Riggs et al. | |
| 5,193,533 A | 3/1993 | Body et al. | |
| 5,197,463 A | 3/1993 | Jeshuran | |
| 5,207,220 A | 5/1993 | Long | |
| 5,217,005 A | 6/1993 | Weinstein | |
| 5,231,983 A | 8/1993 | Matson et al. | |
| 5,233,979 A | 8/1993 | Strickland | |
| 5,246,419 A | 9/1993 | Absten | |
| 5,250,287 A | 10/1993 | Cocozza | |
| 5,255,675 A | 10/1993 | Kolobow | |
| 5,261,892 A | 11/1993 | Bertaud et al. | |
| 5,273,531 A | 12/1993 | Knoepfler | |
| 5,285,778 A | 2/1994 | Mackin | |
| 5,287,847 A | 2/1994 | Piper et al. | |
| 5,287,849 A | 2/1994 | Piper et al. | |
| 5,287,850 A | 2/1994 | Haber et al. | |
| 5,291,882 A | 3/1994 | Makhoul et al. | |
| 5,292,304 A | 3/1994 | Mantell et al. | |
| 5,305,698 A | 4/1994 | Blackwell et al. | |
| 5,313,939 A | 5/1994 | Gonzalez | |
| 5,318,517 A | 6/1994 | Reiman | |
| 5,328,458 A | 7/1994 | Sekino et al. | |
| 5,329,921 A | 7/1994 | Socaris et al. | |
| 5,333,607 A | 8/1994 | Kee et al. | |
| 5,342,299 A * | 8/1994 | Snoke et al. | 604/95.04 |
| 5,360,396 A | 11/1994 | Chan | |
| 5,362,310 A | 11/1994 | Semm | |
| 5,363,839 A | 11/1994 | Lankford | |
| 5,372,131 A | 12/1994 | Heinen, Jr. | |
| 5,383,923 A * | 1/1995 | Webster, Jr. | 607/125 |
| 5,411,474 A | 5/1995 | Ott et al. | |
| 5,411,988 A | 5/1995 | Bockow et al. | |
| 5,433,195 A | 7/1995 | Kee et al. | |
| 5,437,636 A * | 8/1995 | Snoke et al. | 600/139 |
| 5,438,982 A | 8/1995 | MacIntyre | |
| 5,439,441 A | 8/1995 | Grimsley et al. | |
| 5,443,447 A | 8/1995 | Kassis | |
| 5,464,008 A | 11/1995 | Kim | |
| 5,472,435 A | 12/1995 | Sutton | |
| 5,478,837 A | 12/1995 | Rodgers et al. | |
| 5,480,380 A | 1/1996 | Martin | |
| 5,496,408 A | 3/1996 | Motoda et al. | |
| 5,499,625 A | 3/1996 | Frass et al. | |
| 5,514,087 A | 5/1996 | Jones | |
| 5,515,844 A | 5/1996 | Christopher | |
| 5,534,261 A | 7/1996 | Rodgers et al. | |
| 5,537,993 A | 7/1996 | Reichert et al. | |
| 5,542,412 A | 8/1996 | Century | |
| 5,544,648 A | 8/1996 | Fischer, Jr. | |
| 5,554,112 A | 9/1996 | Walbrink et al. | |
| 5,558,668 A | 9/1996 | Lankford et al. | |
| 5,565,241 A | 10/1996 | Mathias et al. | |
| 5,578,305 A | 11/1996 | Franz et al. | |
| 5,579,758 A | 12/1996 | Century | |
| 5,586,974 A | 12/1996 | Martinez et al. | |
| 5,594,987 A | 1/1997 | Century | |
| 5,599,297 A | 2/1997 | Chin et al. | |
| 5,606,789 A | 3/1997 | Century | |
| 5,606,968 A | 3/1997 | Mang | |
| 5,611,336 A | 3/1997 | Page et al. | |
| 5,642,730 A | 7/1997 | Baran | |
| 5,664,560 A | 9/1997 | Merrick et al. | |
| 5,728,223 A | 3/1998 | Murakami et al. | |
| 5,779,669 A * | 7/1998 | Haissaguerre et al. | 604/95.01 |

| | | | |
|---|---|---|---|
| 5,785,706 A * | 7/1998 | Bednarek | 606/41 |
| 5,800,381 A | 9/1998 | Ognier | |
| 5,803,078 A | 9/1998 | Brauner | |
| 5,820,591 A * | 10/1998 | Thompson et al. | 604/95.01 |
| 5,873,819 A | 2/1999 | Koch | |
| 5,934,274 A | 8/1999 | Merrick et al. | |
| 5,964,223 A | 10/1999 | Baran | |
| 5,979,474 A | 11/1999 | Manako | |
| 5,980,835 A | 11/1999 | Porozni | |
| 6,016,800 A | 1/2000 | Century | |
| 6,029,657 A | 2/2000 | Century | |
| 6,041,775 A | 3/2000 | Century | |
| 6,051,241 A | 4/2000 | Briend et al. | |
| 6,068,703 A | 5/2000 | Chen et al. | |
| 6,076,745 A | 6/2000 | Primdahl | |
| 6,079,413 A | 6/2000 | Baran | |
| 6,082,361 A | 7/2000 | Morejon | |
| 6,085,556 A | 7/2000 | Moon | |
| 6,086,529 A | 7/2000 | Arndt | |
| 6,092,364 A | 7/2000 | Stellwagen | |
| 6,102,042 A | 8/2000 | Hete et al. | |
| 6,116,240 A | 9/2000 | Merrick et al. | |
| 6,119,954 A | 9/2000 | Kamath | |
| 6,165,201 A | 12/2000 | Sawhney et al. | |
| 6,203,519 B1 | 3/2001 | Fagerström et al. | |
| 6,227,195 B1 | 5/2001 | Gonda | |
| 6,237,597 B1 | 5/2001 | Kovac | |
| 6,240,943 B1 | 6/2001 | Smith | |
| 6,257,236 B1 | 7/2001 | Dutkiewicz | |
| 6,267,746 B1 * | 7/2001 | Bumbalough | 604/95.01 |
| 6,299,592 B1 | 10/2001 | Zander | |
| 6,322,003 B1 | 11/2001 | Haruch | |
| 6,379,373 B1 | 4/2002 | Sawhney et al. | |
| 6,428,500 B1 | 8/2002 | Koninckx | |
| 6,511,471 B2 * | 1/2003 | Rosenman et al. | 604/528 |
| 6,526,976 B1 | 3/2003 | Baran | |
| 6,537,246 B1 | 3/2003 | Unger et al. | |
| 6,579,278 B1 * | 6/2003 | Bencini | 604/528 |
| 6,579,279 B1 | 6/2003 | Rabiner et al. | |
| 6,595,202 B2 | 7/2003 | Ganan-Calvo | |
| 6,679,873 B2 * | 1/2004 | Rabiner et al. | 604/528 |
| 6,719,960 B1 | 4/2004 | Hills et al. | |
| 6,729,334 B1 | 5/2004 | Baran | |
| 6,802,835 B2 * | 10/2004 | Rabiner et al. | 604/528 |
| 6,973,352 B1 | 12/2005 | Tsutsui et al. | 607/122 |
| 7,027,851 B2 * | 4/2006 | Mejia | 600/374 |
| 7,037,290 B2 * | 5/2006 | Gardeski et al. | 604/95.01 |
| 7,048,711 B2 * | 5/2006 | Rosenman et al. | 604/95.04 |
| 7,377,906 B2 * | 5/2008 | Selkee | 604/95.04 |
| 7,402,151 B2 | 7/2008 | Rosenman et al. | |
| 7,488,305 B2 * | 2/2009 | Mickley et al. | 604/164.12 |
| 7,493,156 B2 * | 2/2009 | Manning et al. | 600/434 |
| 7,494,478 B2 * | 2/2009 | Itou et al. | 604/95.04 |
| 7,497,853 B2 * | 3/2009 | Fischer et al. | 604/528 |
| 7,503,914 B2 * | 3/2009 | Coleman et al. | 604/528 |
| 7,524,301 B2 * | 4/2009 | Dubois et al. | 604/95.04 |
| 2002/0082584 A1 | 6/2002 | Rosenman et al. | |
| 2002/0165461 A1 * | 11/2002 | Hayzelden et al. | 600/523 |
| 2002/0165484 A1 * | 11/2002 | Bowe et al. | 604/95.05 |
| 2002/0165485 A1 * | 11/2002 | Simpson et al. | 604/95.05 |
| 2002/0165534 A1 * | 11/2002 | Hayzelden et al. | 606/41 |
| 2002/0183715 A1 | 12/2002 | Mantell et al. | |
| 2003/0130598 A1 * | 7/2003 | Manning et al. | 600/585 |
| 2003/0149422 A1 * | 8/2003 | Muller | 604/528 |
| 2004/0084049 A1 | 5/2004 | Baran | |
| 2004/0116848 A1 * | 6/2004 | Gardeski et al. | 604/95.01 |
| 2004/0193205 A1 * | 9/2004 | Burgermeister | 606/194 |
| 2004/0260236 A1 * | 12/2004 | Manning et al. | 604/95.04 |
| 2005/0010164 A1 | 1/2005 | Mantell | |
| 2005/0197623 A1 * | 9/2005 | Leeflang et al. | 604/95.04 |
| 2005/0273051 A1 * | 12/2005 | Burgermeister | 600/585 |
| 2006/0135961 A1 * | 6/2006 | Rosenman et al. | 606/108 |
| 2006/0270975 A1 * | 11/2006 | Savage | 604/95.04 |
| 2006/0270976 A1 * | 11/2006 | Savage et al. | 604/95.04 |
| 2007/0265595 A1 | 11/2007 | Miyamoto et al. | |
| 2008/0287918 A1 * | 11/2008 | Rosenman et al. | 604/528 |
| 2009/0125001 A1 * | 5/2009 | Anderson et al. | 604/528 |

FOREIGN PATENT DOCUMENTS

| | | |
|---|---|---|
| EP | 672 273 B1 | 1/1996 |
| EP | 0 937 478 A1 | 8/1999 |
| EP | 0 712 635 B1 | 5/2003 |
| EP | 1 477 119 A1 | 11/2004 |
| FR | 2 840 222 | 12/2003 |
| JP | 5-168714 | 2/1993 |
| JP | 63-84243 | 6/1998 |
| WO | WO 93/17744 | 9/1993 |
| WO | WO 94/00484 | 1/1994 |
| WO | WO 96/29987 | 10/1996 |
| WO | WO 96/40090 | 12/1996 |
| WO | WO 00/69511 | 11/2000 |

OTHER PUBLICATIONS

European Search Report dated Jun. 12, 2008—EP 04798753.2.
U.S. Appl. No. 10/696,675, entitled "Dual-Capacity Insufflator Tube", filed Oct. 28, 2003.
U.S. Appl. No. 10/961,475, entitled "System and Method for Delivering a Substance to a Body Cavity", filed Oct. 7, 2004.

* cited by examiner

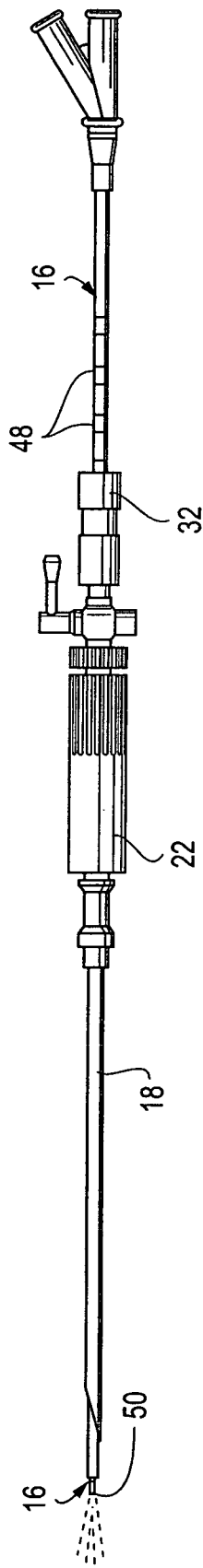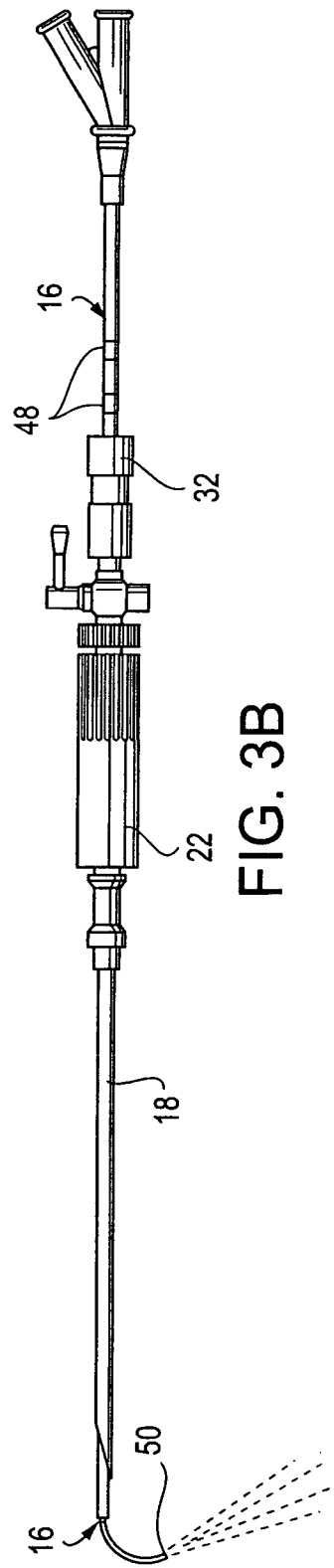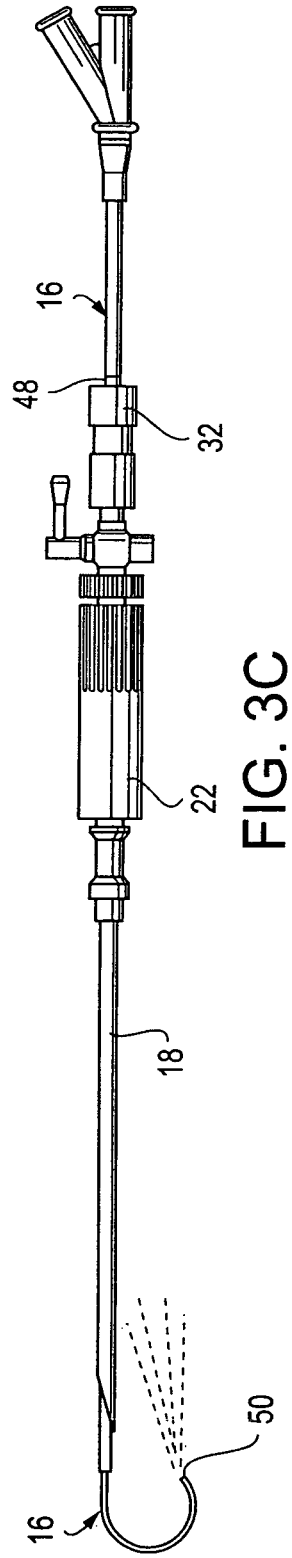

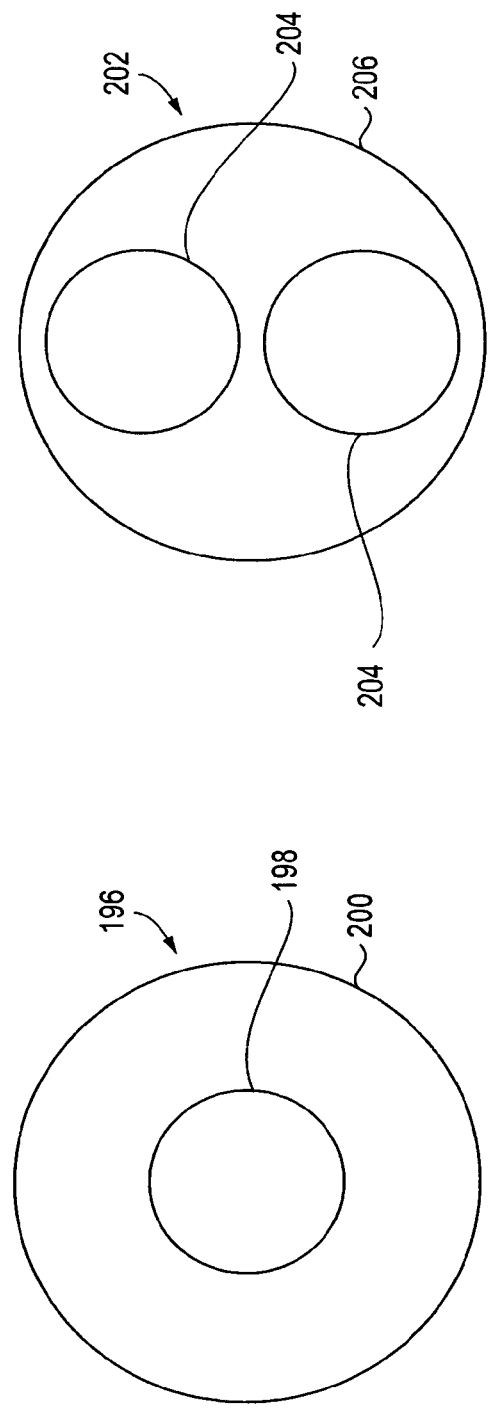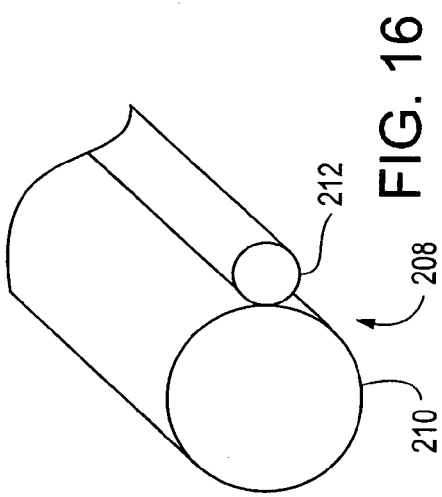

SYSTEM AND METHOD FOR MANIPULATING A CATHETER FOR DELIVERING A SUBSTANCE TO A BODY CAVITY

CROSS-REFERENCE TO RELATED APPLICATION

This application claims the benefit of U.S. Provisional Application No. 60/516,258, filed Oct. 31, 2003 the entirety of which is incorporated herein by reference.

FIELD OF THE INVENTION

The present invention relates to a system and method for manipulating a catheter or tube used to deliver a substance to a body cavity.

BACKGROUND

Recent medical studies suggest that it may be beneficial to deliver therapeutic aerosols or liquid or gas stream to anatomical surfaces within the surgical field of patients that are undergoing open or minimally invasive surgical procedures. In the case of minimally invasive surgery (MIS), the surgical field may be a natural or artificially created body cavity or lumen. Similarly, it may be desirable to deliver therapeutic aerosols to an open anatomical surface. The aerosol formulations may be delivered before a surgical procedure, after a surgical procedure, or in the absence of an adjunctive surgical procedure.

Among problems that physicians have encountered during diagnostic or surgical procedures, using both "open" techniques, and minimally invasive surgical techniques (e.g. laparoscopic), are numerous post procedural complications. These complications can consist of, but are not limited to, post operative pain, infections, tissue adhesions, and tumor formation. Numerous products, such as medications and associated delivery systems, addressing these issues exist on the market to improve the surgical or invasive experience and patient outcomes. Among these products are suction and irrigation wands that are used for flushing tissue sites with sterile water or saline and removing blood. There are medications, which are spread over exposed organs, to coat or provide a barrier between tissue and organs for prevention of adhesions. These materials may be in gel form, sheet form, spray (liquid) form, or aerosol form to coat organs or tissues, or to provide thin layer deposition to the organs in the operative site. Some of these materials may be used in both open and minimally invasive surgical techniques.

A problem with delivering substances to anatomical surfaces in a body cavity is the inability to easily and effectively control delivery to all or a portion of the surgical field. Among the difficulties associated with spraying of liquids, is the pooling and lack of containment of the fluids used with irrigation and aspiration wands. It is also difficult to cover large areas (greater than several square centimeters), and to do so without using much more medicament than is necessary. This contributes to the cost of excessive medication, and adding to the cost and time of the surgery.

In some circumstances it may be desirable to direct aerosol to certain areas within a cavity, particularly the tissue surrounding the entry ports created in a patient's abdomen in order to insert a surgical instrument. The nozzles on many current devices are fixed in orientation with respect to the instrument shaft. As a result, the caregiver must manipulate the shaft to direct the aerosol. This is problematic if the aerosol needs to be directed backward towards the entry point of the shaft, since the end of the shaft is outside the patient, and would need to be positioned in the cavity in order to direct the aerosol towards the inside of the entry port. It may also be problematic during open surgery in circumstances where the spray needs to be directed towards a target site that faces away from the surgical opening, or that is obstructed by an anatomical structure or instrumentation. Although some devices are capable of generating radial aerosol patterns, none are capable of directing an aerosol directly backwards towards the devices point of entry into a surgical cavity.

While some devices have a deflectable tip that allows the user to aim the aerosol, they rely on designs that require a mechanical linkage to bend a hinged tip. These are likely expensive to manufacture due to the mechanical complexity involved.

The spray particles produced by current delivery devices are often quite large and have a high exit velocity from the nozzle. As a result, they have a high inertia due to their relatively large mass and the speed with which they exit the aerosol generation nozzle. The particles tend to travel in a straight line and immediately impact upon the surface in front of them, creating an inertial deposition pattern. In addition, aerodynamic factors cause these larger particles to fall more rapidly than a smaller aerosol. This creates a gravity dependent deposition pattern which preferentially coats the lower surfaces of the cavity. This is problematic when a uniform, even deposition of aerosol is required on the top, bottom, and sides of the surgical cavity. Finally, the large and rapidly moving particles may cause trauma if the nozzle is positioned too close to sensitive tissue.

During a minimally invasive surgical procedure within a body cavity or lumen it may not be possible or convenient to visually determine the location and direction of the aerosol generation nozzle. As a result it may be difficult to determine which part of the cavity the aerosol is directed at. It may also be difficult to systematically manipulate the aerosol nozzle in a pattern that creates a uniform deposition of aerosol on all cavity surfaces.

BRIEF SUMMARY

In order to address the deficiencies in the prior art, a system and method of controllably applying a substance to a body cavity for the purpose of treating or coating tissues and/or organs, and for use in the minimally invasive surgical procedures is described. The term "substance", as used in this specification, includes, without limitation, a liquid, powder, gas, light, such as laser or ultraviolet (UV) light, or any combination thereof. The term "body cavity", as used in this specification, includes without limitation, body cavities created through introduction of a gas into the body, as well as naturally occurring cavities in the body or organs in the body. According to a first aspect of the invention, a system for manipulating a catheter for delivering a substance to a body cavity of a patient is disclosed comprising a catheter having at least one lumen where the proximal end of the catheter is configured to receive a substance intended for delivery to a body cavity. A distal end of the catheter includes a flexible tip biased in a pre-shaped orientation. An introducer apparatus for guiding the catheter includes a body defining a bore sized to receive the catheter, and a catheter adjustment mechanism releasably connectable with the catheter. The catheter adjustment mechanism is movable relative to the body of the introducer apparatus and is manually adjustable to control at least one of rotational and axial movement of the catheter relative to the body of the introducer apparatus.

According to another aspect of the invention, a method for manipulating a catheter for delivery of a substance to a body cavity is disclosed. The method includes inserting an introducer apparatus into a body cavity through a boundary of the body cavity and introducing a catheter into the body cavity through the introducer, wherein the catheter comprises a distal portion having a nozzle positioned on a flexible tip biased in a predetermined shape. The catheter is axially moved with respect to the introducer apparatus such that the predetermined shape of the flexible tip is altered and such that an angle of the nozzle is altered from an original angle. The catheter shaft is rotated with respect to a first portion of the introducer apparatus through rotation of a second portion of the introducer apparatus operably connected with the catheter shaft so that a rotational orientation of the nozzle in the body cavity is altered. Also, a substance is provided to the body cavity through the catheter.

BRIEF DESCRIPTION OF THE DRAWINGS

FIG. 3A is a side view of the system of FIG. 1 with the tip of the catheter retracted to a fully retracted position in the introducer apparatus.

FIG. 3B is a side view of the system of FIG. 1 with the tip of the catheter retracted to a partially retracted position.

FIG. 3C is a side view of the system of FIG. 1 with the tip of the catheter positioned in a fully inserted position.

FIG. 14 is a cross-sectional view of a first alternative catheter structure suitable for use in the embodiments of FIGS. 1, 4 and 8.

FIG. 15 is a cross-sectional view of a second alternative catheter structure suitable for use in the embodiments of FIGS. 1, 4 and 8.

FIG. 16 is a perspective sectional view of a third alternative catheter structure suitable for use in the embodiments of FIGS. 1, 4 and 8.

DETAILED DESCRIPTION OF THE PRESENTLY PREFERRED EMBODIMENTS

Figure 1:
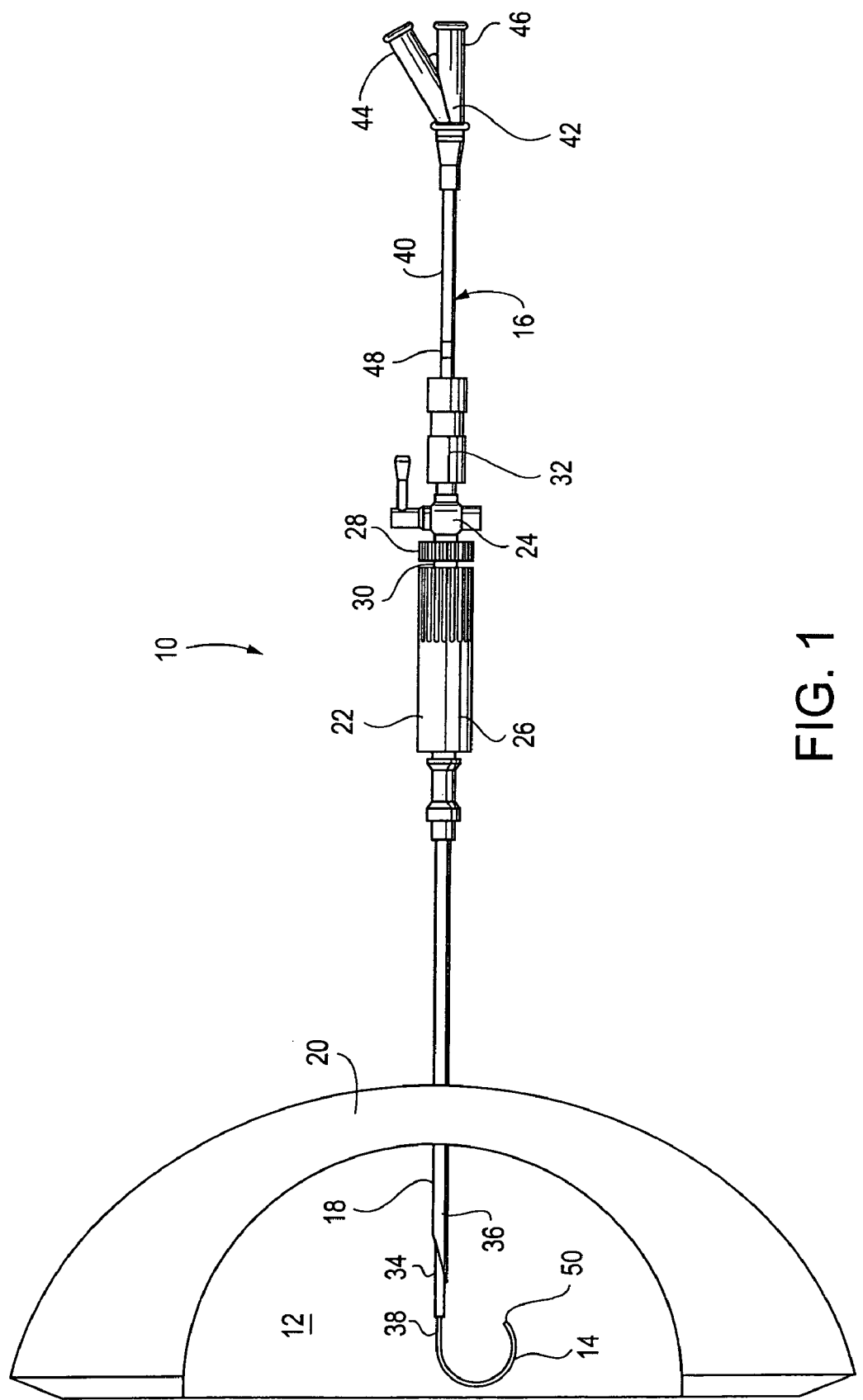
FIG. 1 is a side view of a system for manipulating a catheter inserted in a body cavity according to an embodiment of the present invention.
Figure 2:
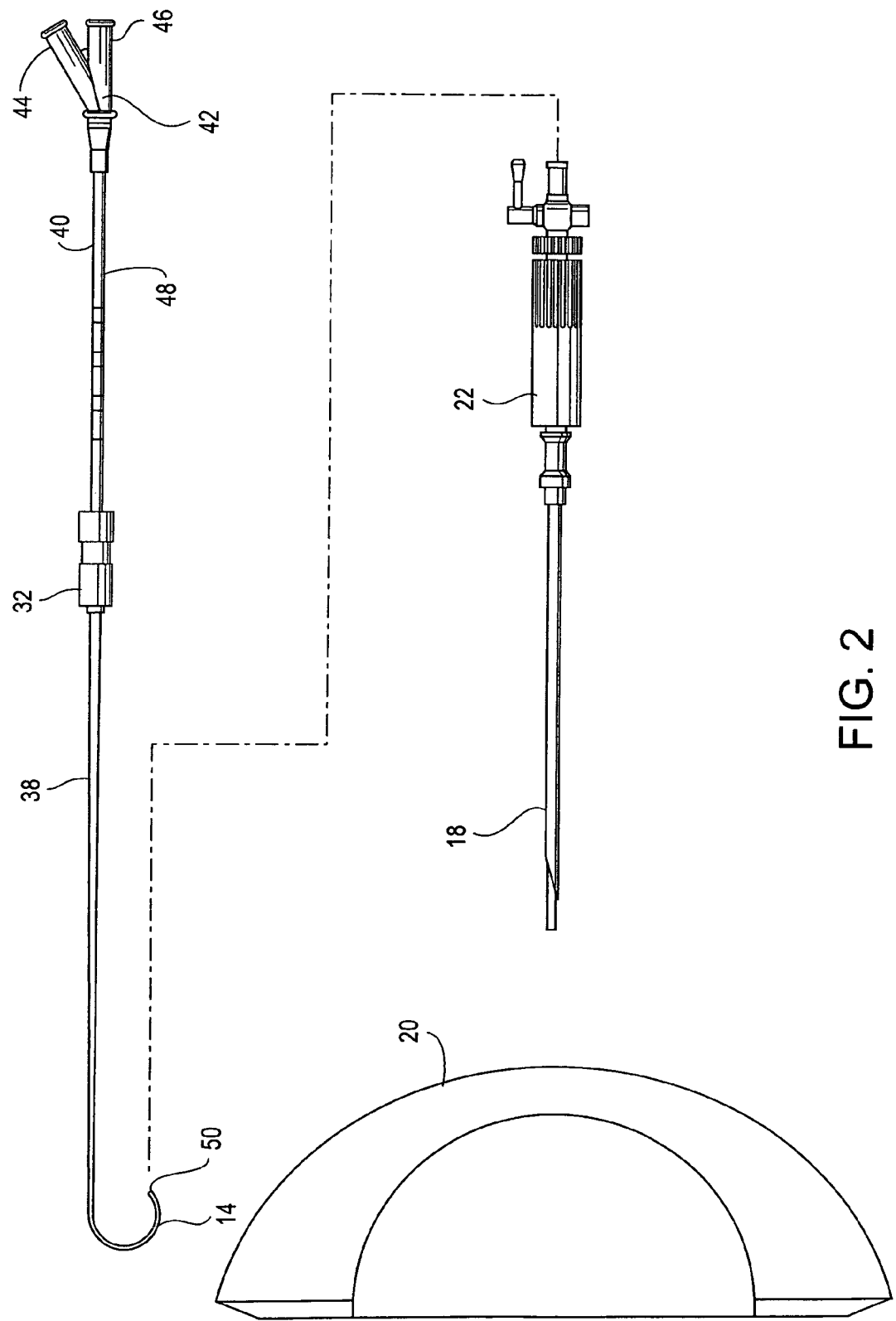
FIG. 2 is an exploded view of the system of FIG. 1.

Referring to FIGS. 1-2, an embodiment of a system 10 for delivery of a substance to a body cavity 12 is shown with a shaped distal end 14 of a catheter 16 positioned in the body cavity via an introducer needle 18 piercing an abdominal wall 20. An introducer apparatus 22 releasably connects with the introducer needle 18 on one end and a valve 24 at the opposite end. The introducer apparatus 22 is composed of a first body portion 26 rotatably connected with a rotational adjustment ring 28. The rotational adjustment ring 28 may be rotatably connected with the first body portion 26 by any of a number of known frictional-fit, bearing or other adjustable rotational coupling arrangements. In one embodiment, an O-ring 30 is positioned between the first body portion 26 and rotational adjustment ring 28 to prevent leakage of any fluids. The rotational adjustment ring 28 removably attaches to the valve 24 so that the rotational adjustment ring 28 and valve 24 do not rotate with respect to one another. The valve 24 is configured to releasably connect with an adaptor 32 coupled along a portion of a shaft of the catheter 16.

The introducer needle 18 may be any of a number of types of known needles, such as a Verres needle having a spring loaded retractable portion 34 that retracts into an insertion shaft 36, or other introducing devices. The valve 24 may be a ball valve or any other valve suitable to seal off the end of the introducer apparatus 22 upon removal of the catheter 16, and that can releasably connect to the adaptor 32. The adaptor may be any of a number of adaptors, such as a Touhy-Borst adaptor, suitable for connecting different portions of catheter tubing together. The adapter 32 may include any number of adjustable of fixed sealing arrangements configured so that enough friction is maintained against the outside of the catheter to permit rotational positioning of the catheter by the introducer apparatus 22 in an accurate and repeatable manner, while allowing for longitudinal movement of the catheter through the introducer. Also, the adapter 32 may maintain a seal around the outside of the catheter sufficient to prevent fluid from leaking from the introducer back toward the proximal end of the catheter. The valve 24, introducer apparatus 22 and introducer needle 18 are all preferably sized to cooperate and form a central bore sized to receive a catheter or other tubing assembly.

Figure 25:
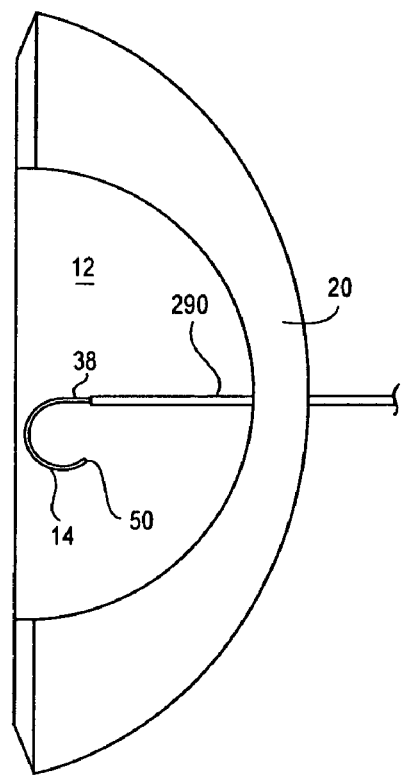
FIG. 25 illustrates a sleeve comprising a blunt-ended single lumen without any retractable components for use with the introducer and catheter adjustment mechanism of FIGS. 1-3.

In other embodiments, as shown in FIG. 25, the introducer needle 18 may be replaced by any of a number of blunt-ended, single lumen sleeves 290 that consist of a hollow tube sized to receive the catheter. The sleeve 290 does not have concentrically arranged outer portion and retractable inner portion as discussed with respect to the Verres needle embodiment above. Preferably, the sleeve 290 has a rigidity greater than that of a pre-shaped catheter with a curved portion, and the catheter will bend only after it protrudes from the tip of the sleeve a desired distance (i.e., so that the sleeve does not bend or curve due to any pre-shaped curve in the catheter). The blunt-ended sleeve 290 may be used, for example, where an entry port into the cavity already exists. Also, the inner diameter of the sleeve 290 may be only slightly greater than the outer diameter of the catheter so that the catheter maintains the ability for smooth longitudinal movement and will not bend within the sleeve when inserted into a body cavity.

The catheter 16 consists of a tapered section 38 toward the distal end and a proximal portion 40 accessible for axial adjustment of the catheter. The proximal portion 40 connects with a catheter hub 42 positioned into a catheter gas port 44 and a catheter liquid port 46. The proximal portion 40 of the catheter 16 includes one or more catheter markings 48. The catheter markings are spaced apart at even intervals in one embodiment. Catheter markings 48 may be spaced apart at uneven intervals in other embodiments. The catheter markings may consist of bands of the same or different colors, may include indicia indicative of an insertion depth or orientation of the distal end of the catheter, or may consist of one or more different texture regions. The texture regions may be uniform or may consist of differing shapes or configurations (e.g. raised or recessed regions). Any of a number of other forms of indicia is also contemplated.

In one embodiment, the pre-shaped tip 14 of the catheter 16 is curved or angled such that retraction of the catheter 16 through the needle 18 by pulling on the proximal portion 40 will cause the pre-shaped tip 14 to change its angle orientation. Referring to FIGS. 3A-3C, the method of adjusting the angle of the tip of the catheter by withdrawing the proximal portion 40 of the catheter 16 with respect to the adaptor 32 is shown. In FIG. 3A, the pre-shaped tip 14 of the catheter is shown in its fully retracted position where the curve or bend is completely eliminated and any aerosol is ejected from the system 10 in a substantially longitudinal direction. In this position, the proximal portion 40 of the catheter is in its greatest extension revealing the largest number of catheter markings 48.

In FIG. 3B, the catheter is shown in a partially retracted position where the proximal portion 40 of the catheter has been further inserted through the adaptor 32 such that the pre-set curve of the distal end has partially reasserted itself and aerosol is ejected from the system at an angle between that of the fully retracted position of FIG. 3A and the fully inserted catheter position of FIG. 3C. In FIG. 3C, the pre-shaped tip returns to its original resting state and directs aerosol back towards the proximal end of the system such that tissue surrounding the insertion points of the introducer needle 18 may also be coated with a substance delivered by aerosol. At each of the various insertion levels, the rotational adjustment wheel 28 of the introducer apparatus may be used to rotationally position the tip 14 of the catheter so that the catheter nozzle 50 may be adjusted in any position along a 360 degree path at various insertion depths of the catheter 16. Intermediate positions of catheter retraction, and thus differing angles of the nozzle 50 may be used to direct the aerosol in relation to the introducer port between the entirely forward orientation of the fully retracted arrangement shown in FIG. 3A and the entirely backward, or proximal, orientation of the catheter nozzle as shown in the fully inserted configuration of FIG. 3C. The controllable tip angle, combined with the adjustable rotational orientation, may be used to create even spherical application of substances onto the body cavity, or controlled application of a substance to a portion of the body cavity.

The catheter 16 may be constructed with a single lumen or multiple lumens. In multiple lumen arrangements, one or more of the lumens may be dedicated to a nebulizing gas and the other of the lumens may be dedicated to carrying a liquid or other substance. Although a catheter is shown in FIGS. 1-3, a simple tubing assembly, with or without taper, may be substituted. Preferably, any catheter or tubing assembly would include a pre-shaped tip, whether angled or curved, with an orientation that is adjustable by retracting all or a portion of the tip through the end of the introducer needle. In the embodiment of FIGS. 1-3, the longitudinal position of the catheter is independently adjustable by manually pushing or pulling the proximal end of the catheter through the catheter hub 32, and thus adjusting the angle of the pre-shaped tip 14, independently of the rotational adjustments of the catheter obtained by rotating the rotatable adjustment ring 28 on the introducer apparatus 22 with respect to the first body portion 26.

The catheter may be formed of any of a number of flexible materials, such as a nylon. A shaped spring wire or other type of resilient reinforcing shaft may be inserted or embedded in the full catheter shaft and/or tip area to create the intended shape. Alternatively, the polymer or catheter material may be selected and manufactured to impart a resilient shape or curve without the need for a reinforcing member. One suitable type of catheter adaptable for use in the system 10 is described in U.S. Pat. No. 5,964,223, the entirety of which is incorporated herein by reference.

An alternative embodiment of the system of FIGS. 1-3 is illustrated in FIGS. 4-7. Rather than permit independent longitudinal and rotational movement of the catheter, the embodiment of FIGS. 4-7 illustrates a system 60 incorporating a screw apparatus 62 on the catheter 64 configured to cooperate with a threaded adaptor 66. The threaded adaptor 66 connects with the introducer apparatus 68 via the valve 70. Similar to the embodiment of FIGS. 1-3, an introducer needle 72 provides an entry port for a pre-shaped tip 74 of the catheter 64 through an abdominal wall 20, or other body cavity boundary, and into the body cavity 12. The catheter may be a nebulizing catheter having a catheter liquid port 76 and the catheter gas port 78 meeting at a hub 80.

Unlike the embodiment of FIGS. 1-3, the system 60 of FIGS. 4-7 can combine the longitudinal and rotational movement of the catheter, and thus the pre-shaped tip 74 of the catheter, into a spiral or helical pattern by virtue of the threads 82 on the screw apparatus in cooperation with the complimentary receiving threads in the threaded adaptor 66 attached to the introducer 68. A user may rotate the threads 82 by turning the knob 84 to move the catheter longitudinally and rotationally in the body cavity 12. Preferably, the threads 82 and knob 84 of the screw apparatus 62 are fixedly attached to the catheter shaft 64 so that the catheter will rotate and move longitudinally with the screw apparatus 62. Rotating a proximal end of the catheter shaft using the knob and thread will cause a catheter to advance or retract within the introducer sheath and change the deflection of the curved tip as spirals in thread. This can create a uniform spherical pattern of aerosol within the body cavity as the catheter spirals into or out of the body cavity without the need for visual confirmation, and can improve the repeatability of accurate coating of a body cavity interior. In other embodiments, the functional elements of the screw apparatus 62 and threaded adapter 66 may be formed as part of, or fit within, the insertion apparatus 68. Each of the above-mentioned embodiments of an introducer apparatus and catheter adjustment means may be fabricated from metal components, plastic components, a combination of metal and plastic components, or other suitable materials.

Figure 7:
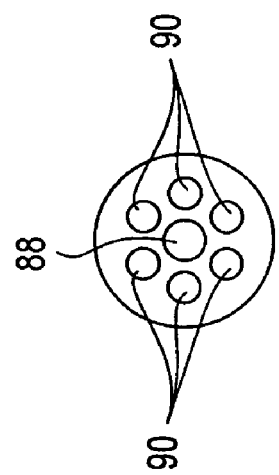
FIG. 7 is an end view of the tip of the catheter of the system of FIGS. 4-5.

FIG. 7 illustrates one of a number of liquid and gas orifice configurations at the nozzle 86 of the pre-shaped tip 74 on the catheter. In this embodiment, a central liquid orifice 88 is encircled by a plurality of gas orifices 90. The gas and liquid orifices may be aligned such that the gas and liquid introduced into the catheter at the gas port and liquid port interact upon exiting through the gas and liquid orifices to form an aerosol. In other embodiments, different numbers and arrangements of orifices may be used. Additionally, a single lumen with a single orifice may be used.

Figure 8:
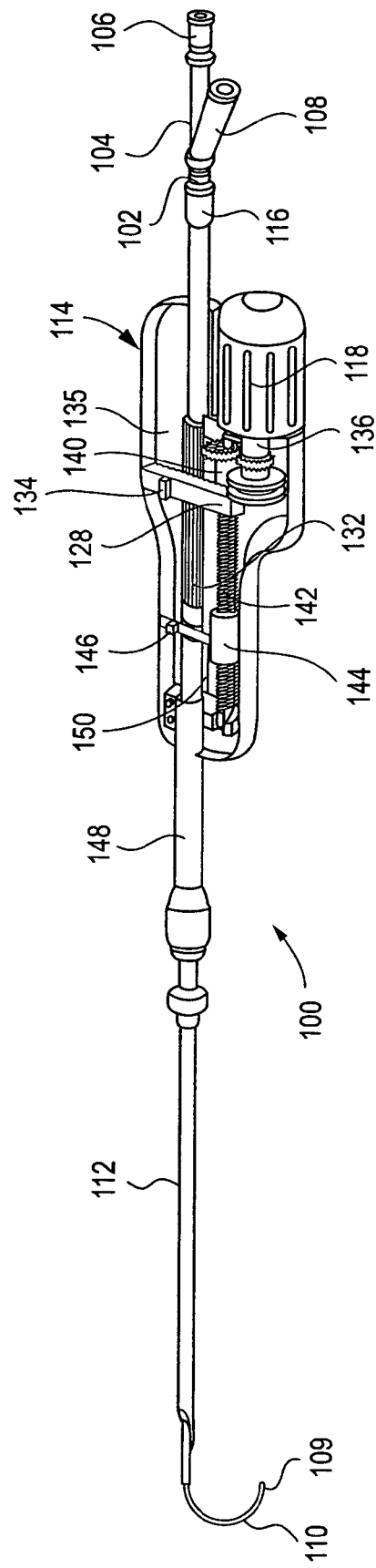
FIG. 8 is a perspective sectional view of a second alternative embodiment of the system of FIG. 1
Figure 9:
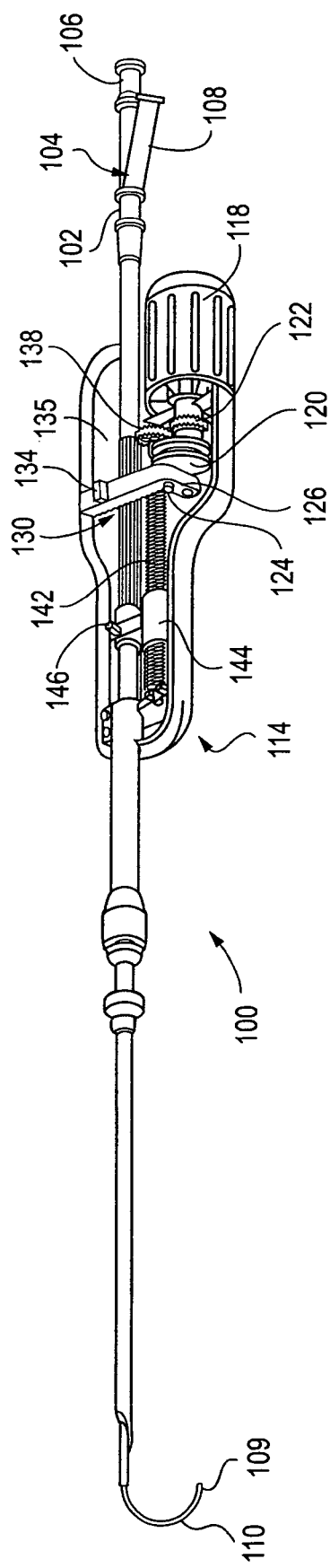
FIG. 9 is an alternate perspective view of the embodiment of FIG. 8.

Another embodiment of a system 100 for manipulating a catheter or other tube to deliver a substance to a body cavity is shown in FIGS. 8-9. In this embodiment, an aerosol exiting the nozzle 109 at the catheter tip 110 may be directed in spherical pattern within the body cavity without the need for independent manipulation of longitudinal and horizontal catheter nozzle positions, such as in the embodiment of FIGS. 1-3, and without the use of a longitudinally and rotationally movable knob such as shown in the embodiment of FIGS. 4-7. In the system 100 of FIGS. 8-9, a gear mechanism of the manipulation apparatus 114 synchronizes longitudinal and horizontal nozzle positioning to produce a spherical aerosol coverage pattern in response to a user's rotation of a single longitudinally fixed knob 118 located near the proximal end of the catheter 102.

The system 100 includes the catheter 102 with a "Y" port assembly 104 having a liquid port 106 and a gas port 108. The liquid and gas ports are connected to lumens extending to the nozzle 109 at the pre-shaped tip 110 of the catheter. An introducer needle 112 or other sheath is provided to introduce the catheter into a body cavity or lumen. The proximal end of the introducer needle 112 is connected to the manipulation apparatus 114. The proximal end of the catheter shaft enters the manipulation apparatus 114 through an entry port 116 and extends through to the distal end of the manipulation apparatus 114 where it continues through the introducer needle 112. The manipulation apparatus 114 includes a knob 118 that may be rotated by a user. Rotation of the knob 118 results in rotation of a boss 120 and gear 122. Rotation of the boss 120 results in circular movement of an offset pin 124 positioned with a slot 126 of a gear rack 128. Movement of the offset pin 124 within the slot 126 causes a reciprocal longitudinal movement of the gear rack 130. The teeth of the gear rack 130 engage and rotate a rotational positioner gear 132 permanently attached to, or integrally formed with, the catheter shaft. Rotational movement of this gear causes the catheter shaft and nozzle to rotate up to 360 degrees in alternate clockwise and counterclockwise directions, thereby directing the aerosol exiting the tip 110 in a spiral or helical pattern. A position indicator tab 134 located on the gear rack 130 corresponds to the rotational position of the catheter tip. This tab 134 may be visualized through a transparent section of housing 135 or, in other embodiments, may extend through a slot in the housing to allow convenient visualization. For convenience and illustration purposes, a top portion of the housing has been omitted so that the gear mechanism is clearly shown. Once fully assembled, the entire gear assembly with the exception of the knob 118 may be fully enclosed. Alternatively, as mentioned above, the position indicator tab 134 and tab 146 may be visualized through a transparent portion of a housing or may extend through an opening in the housing.

Rotation of the knob 118 also results in rotation of the pinion gear 122 that is attached to the input knob shaft 136. The pinion gear 122 engages and rotates a spare gear 138 that is attached to, or formed integrally with, a shaft 140 or worm gear 142 assembly. Rotation of the worm gear 142 causes longitudinal movement of a worm follower 144 and indicator 146. The indicator 146, similar to the position indicator 134 may be visually apparent through a transparent section of the housing or may extend through a slot in the housing to allow convenient visualization. The output connection 148 with a sliding seal perceives the catheter positioner 150 that extends coaxially through the output connection sleeve.

A fixed, or spring-loaded retractable, sheath may be coaxially located between the catheter and introducer needle, or other introducer device. This sheath may be rotationally and/or axially movable in relation to the introducer device. The spiral screw apparatus illustrated in FIGS. 4-6 may be incorporated between this sheath and the introducer device. This allows advancement or retraction of the catheter within the body cavity while maintaining the same degree of tip deflection in relation to the end of the sheath. This may permit the catheter tip to be positioned at various distances away from the entry port while providing the ability to achieve any degree of tip deflection. This may provide flexibility to point the aerosol plume at any surface within the body cavity, including, without limitation, the entry side of the cavity, while at the same time varying the distance of the aerosol nozzle from the surface. This may be advantageous because the aerosol has more force, is more concentrated, and it is expelled in a narrower pattern near the nozzle. A more diffused pattern and gentler force is produced as the aerosol moves away from the nozzle. This adjustment method may be beneficial for selectively applying an intense aerosol in certain area, for example to flush debris or to heavily coat an instrument entry port side. Alternatively, this adjustment method using the combined elements of FIGS. 4-6 and FIGS. 8-9 without adjustments to apply a gentler and more diffused aerosol when targeting delicate tissue.

Figure 10:
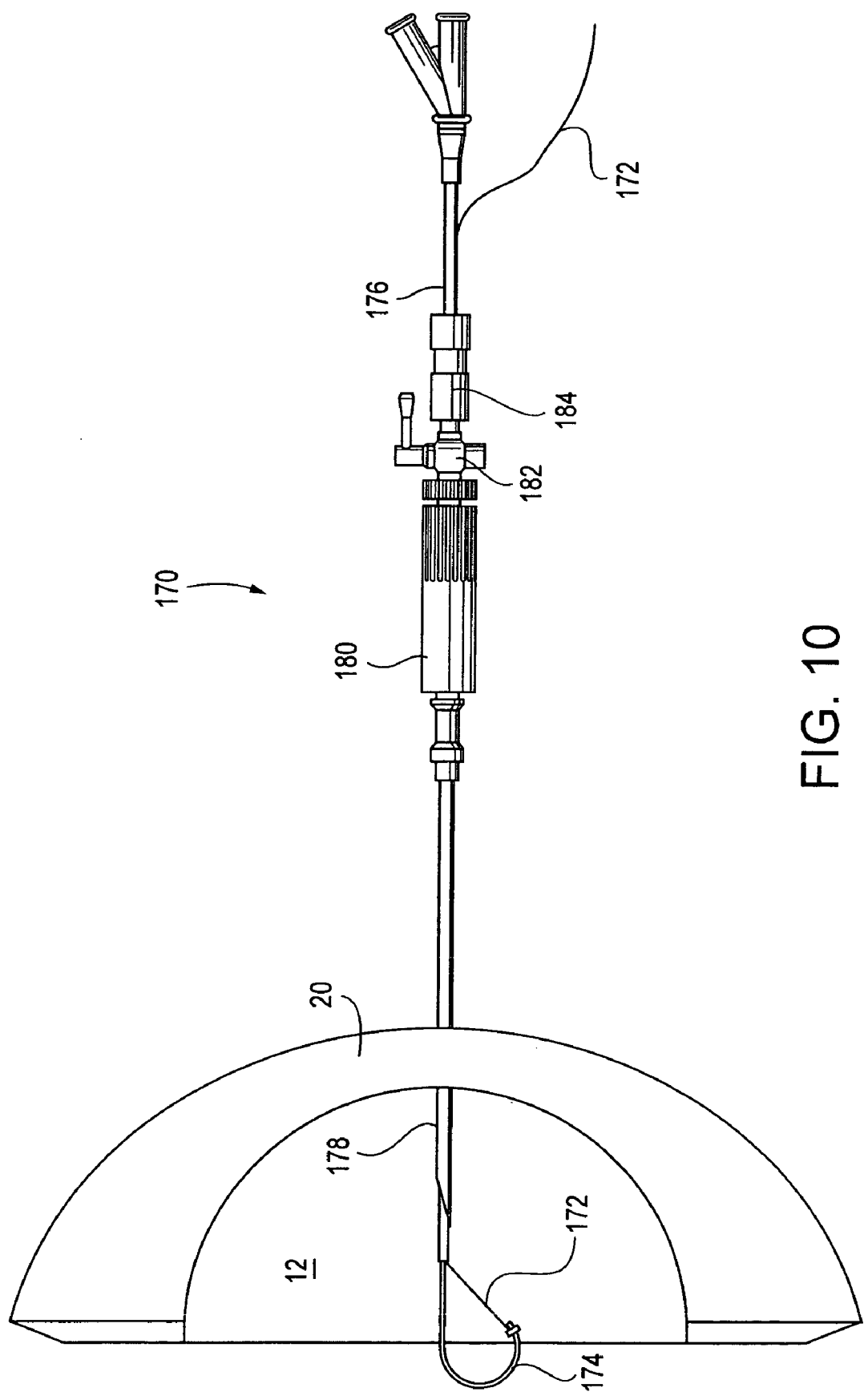
FIG. 10 is a side view of a third alternative embodiment of the system of FIG. 1.
Figure 11:
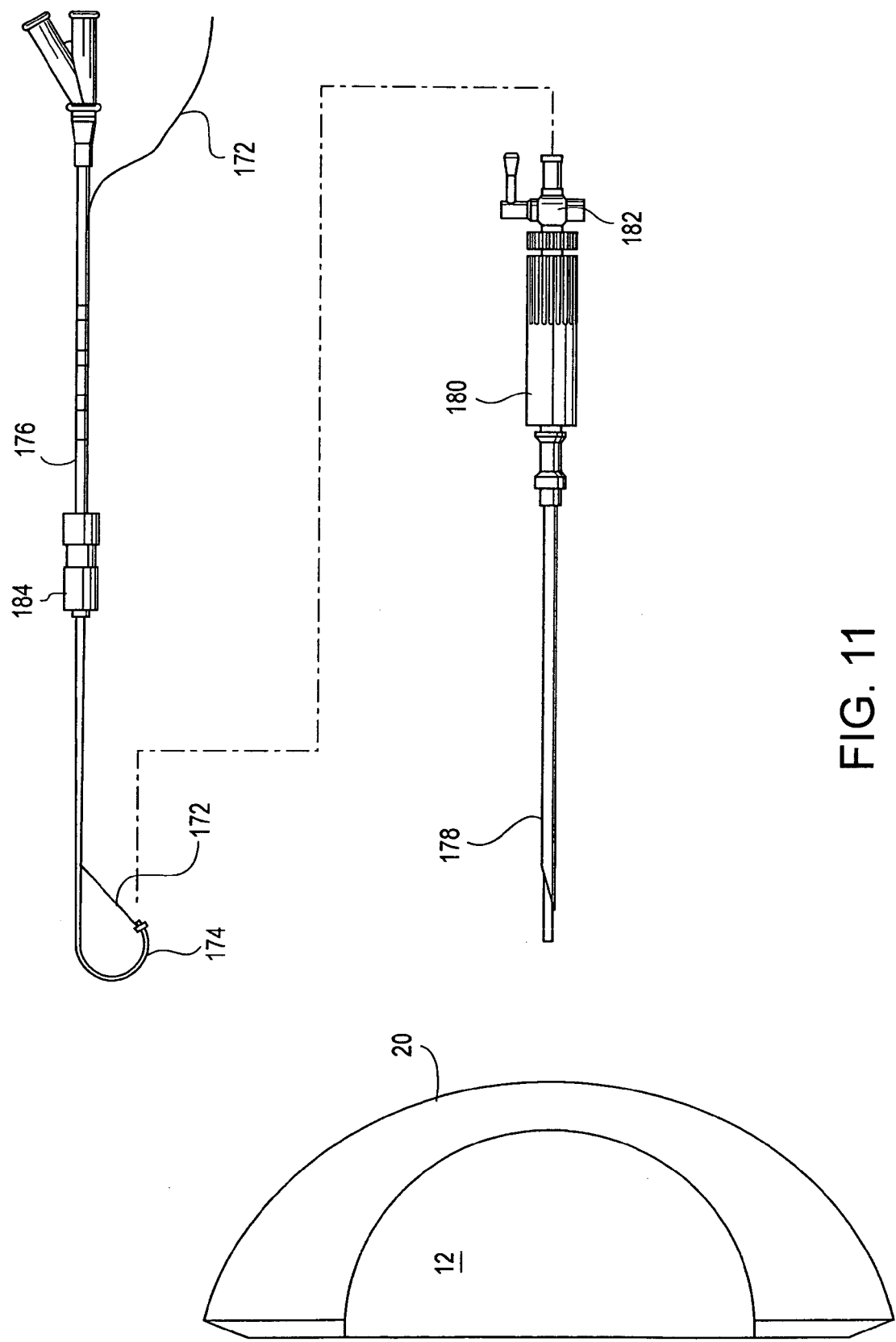
FIG. 11 is an exploded view of the embodiment of FIG. 10.

In another alternative embodiment, as shown in FIGS. 10-11, a system 170 using a positioning string or wire 172 may provide an additional level of adjustability of the direction of a nozzle on the tip 174 of the catheter 176. The movable tensioning wire or member 172 may be contained within the catheter or instrument shaft, entering at the proximal end and exiting at a point toward the distal end, or may be positioned external to the catheter or instrument shaft and extend through the introducer apparatus in parallel with the catheter shaft. The catheter shaft or catheter tip may also be pre-formed in a curved or straight shape and may be deflected by advancing or retracting the straight or resilient wire or member 172 through it. Thus, in this embodiment, the tip of the catheter may be deflected without the use of longitudinally adjusting the position of the entire catheter to leverage against the introducer needle 178 or other type sheath. As illustrated in FIG. 10, the movable tensioning wire or member 172 may be attached adjacent to the nozzle at the distal end of the catheter. The introducer apparatus 180, valve 182 and catheter adapter 184 may be the same as discussed in the embodiments of FIGS. 1-3.

All of the above embodiments may be used with a variety of types of catheter spray nozzles, including, without limitation, non-pneumatic spray nozzles and other pneumatic or pressurized propellant assisted designs such as those disclosed in U.S. Pat. Nos. 5,642,730; 6,079,413; and 5,964,223, wherein the entirety of each of these references is herein incorporated by reference. Nozzle design capable of producing non-conical spray patterns, and the manipulation features that have been discussed above, may be synergistically combined with the various spray nozzle patterns to produce and facilitate controlled, shaped spray deposition patterns that can be optimized for various medical indications, procedures or anatomical applications.

Figure 12:
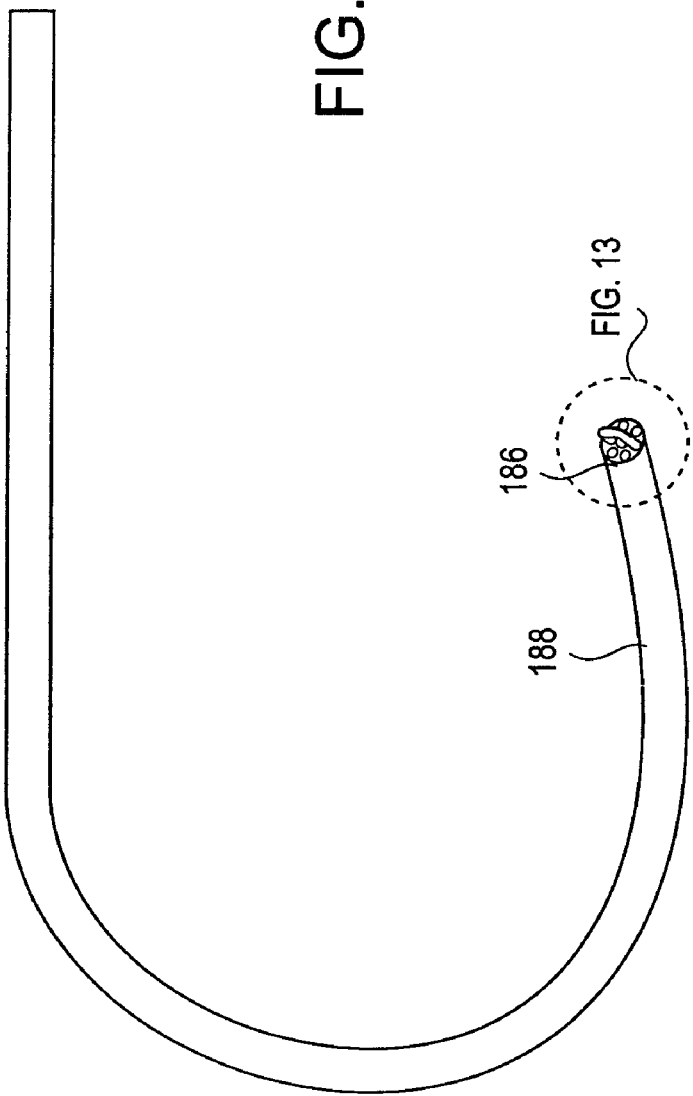
FIG. 12 is an embodiment of a distal end of a catheter suitable for use in the embodiments of FIGS. 1, 4 and 8.
Figure 13:
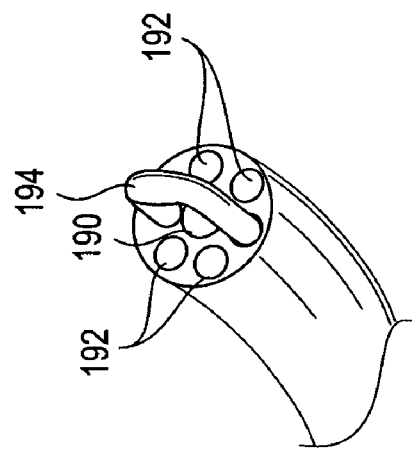
FIG. 13 is a magnified sectional view of the nozzle of the catheter of FIG. 12.

One example of an alternate nozzle arrangement is illustrated in FIGS. 12-13. In this example, the catheter nozzle 186 at the ends of the tip 188 of the catheter shaft produces two radial spray cans that are perpendicular to the catheter shaft. This particular new radial can pattern is achieved by positioning a gas deflector 194 across the central gas orifice 190 and positioning one or more liquid orifices 192 on opposite sides of the gas orifice 190 and gas deflector 194.

Figure 4:
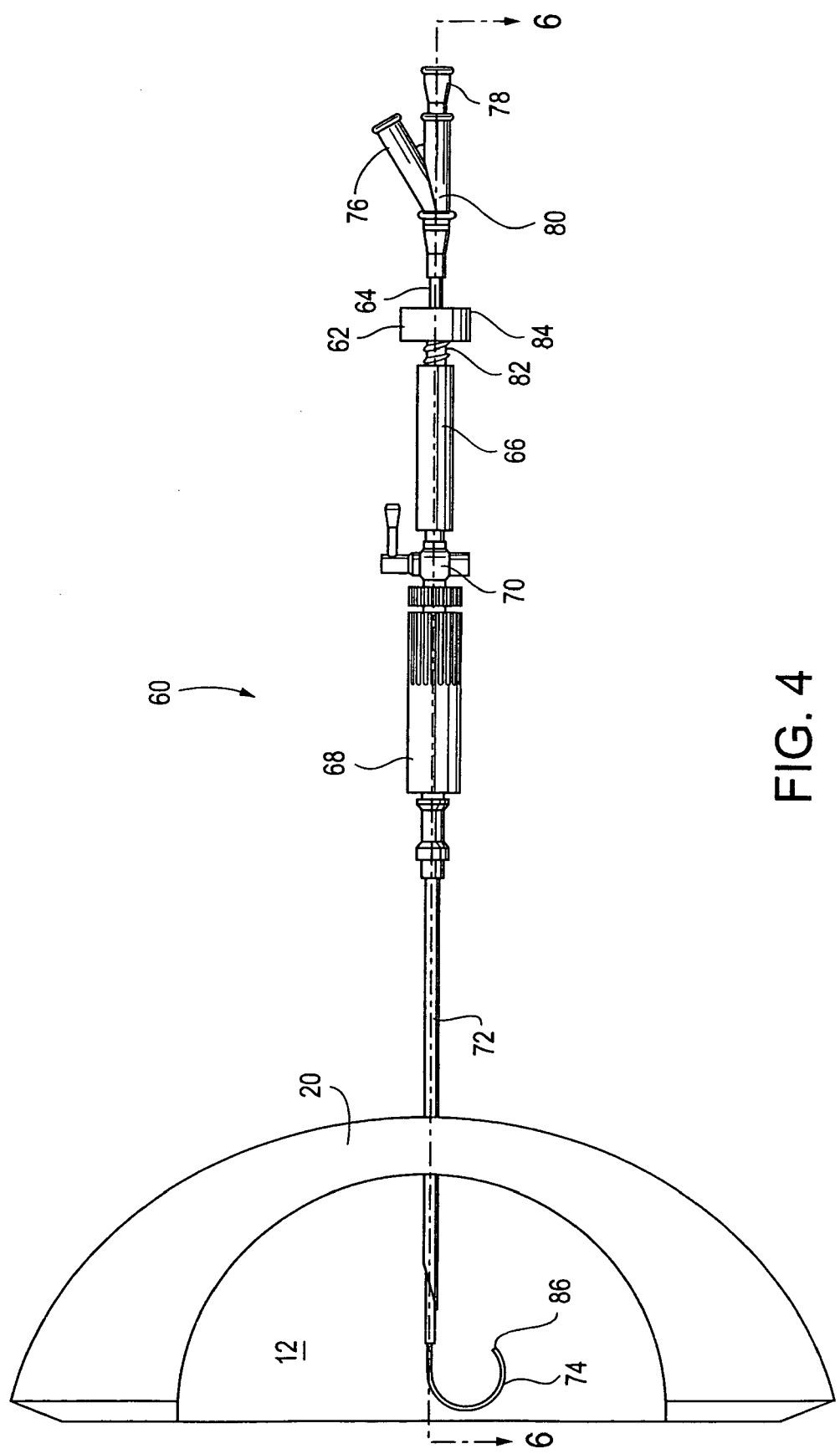
FIG. 4 is a side view of an alternative embodiment of the system of FIG. 1.
Figure 5:
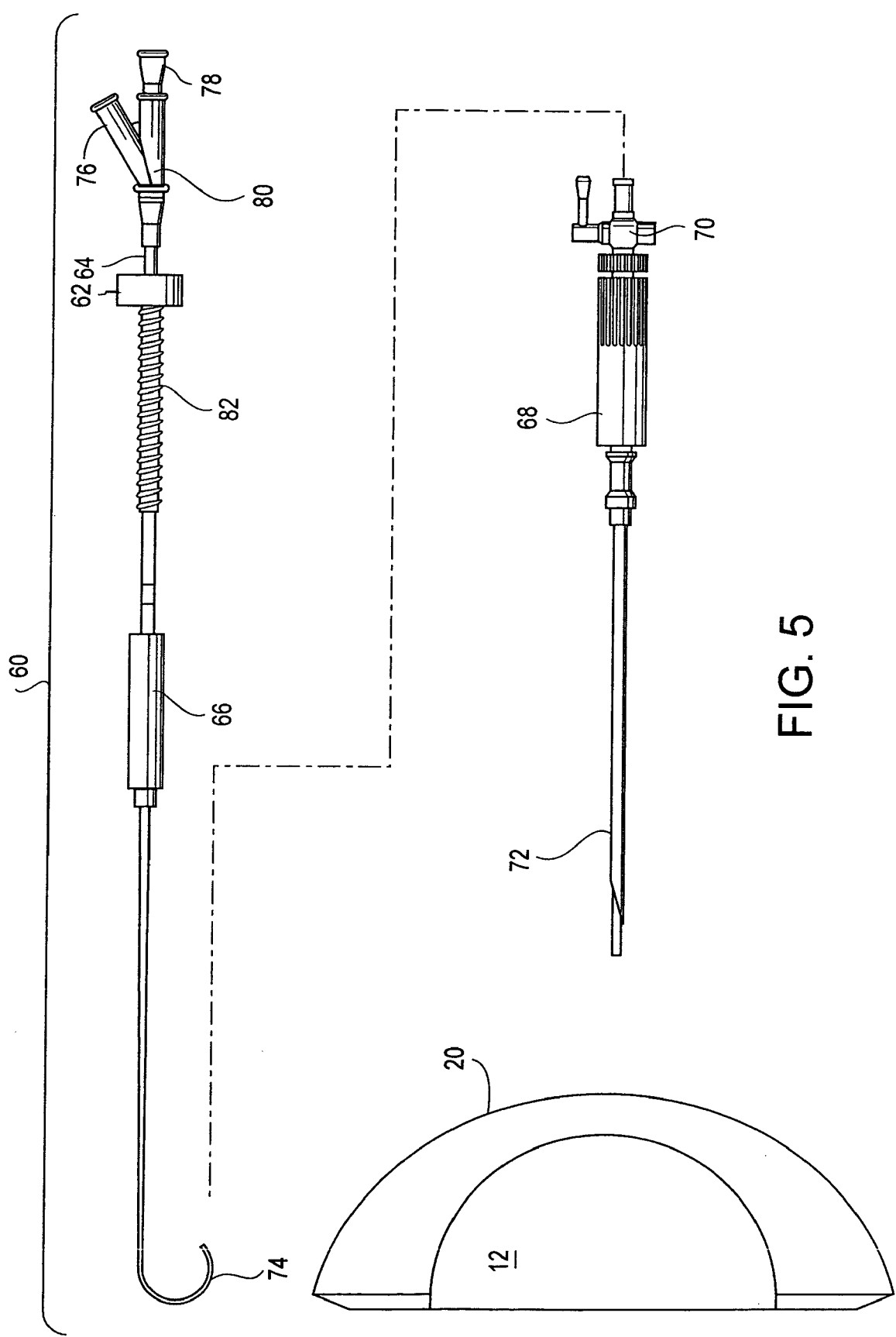
FIG. 5 is an exploded view of alternative embodiment of the system of FIG. 1.
Figure 6:
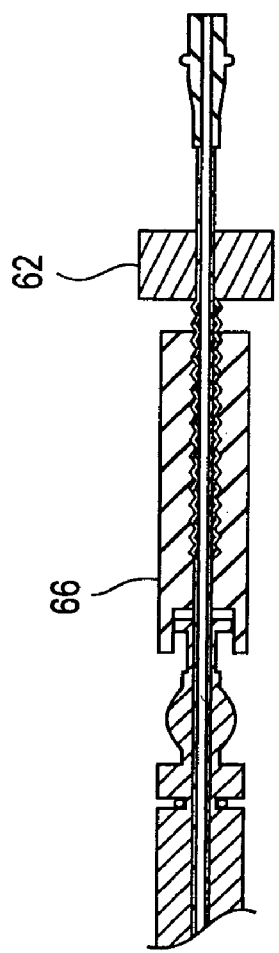
FIG. 6 is a partial cross-sectional view taken along 1-1 of FIG. 4.

FIGS. 14-19 illustrate several of the alternative catheter structures that are contemplated for use in the systems of FIGS. 1, 4 and 8. A catheter 196 may be arranged in a coaxial fashion with an inner tube 198 and outer tube 200, where a liquid is carried inside the inner tube and a gas carried between the inner and outer tubes as shown in FIG. 14. A variation of this is illustrated in FIG. 15, where a catheter 202 has two separate tubes 204 aligned substantially in parallel inside a single outer tube 206. Departing from the coaxial style, FIG. 16 illustrates a catheter 208 comprised of two or more tubes 210, 212 that are bonded or fastened to each other.

Figure 18:
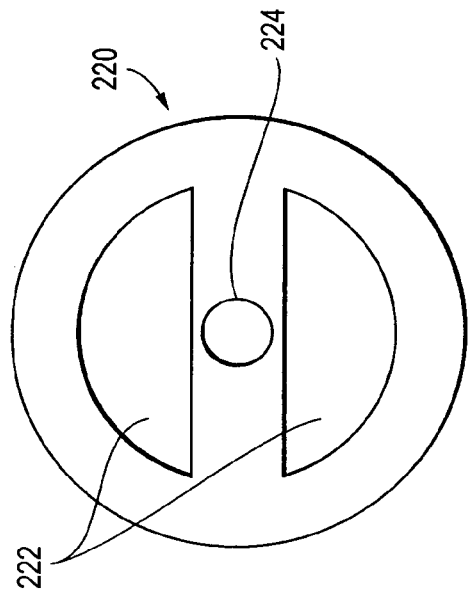
FIG. 18 is a cross-sectional view of a fifth alternative catheter structure suitable for use in the embodiments of FIGS. 1, 4 and 8.
Figure 19:
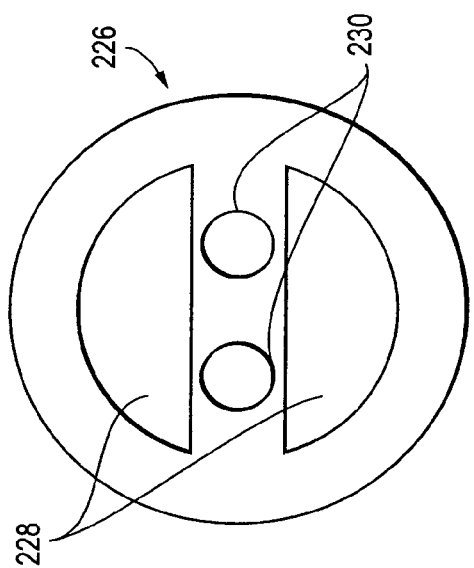
FIG. 19 is a cross-sectional view of a sixth alternative catheter structure suitable for use in the embodiments of FIGS. 1, 4 and 8.
Figure 17:
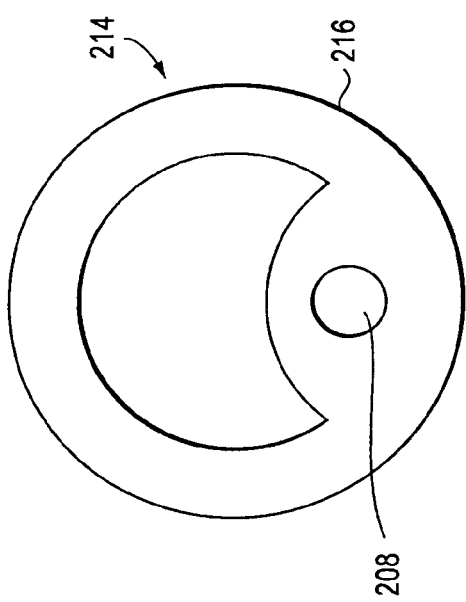
FIG. 17 is a cross-sectional view of a fourth alternative catheter structure suitable for use in the embodiments of FIGS. 1, 4 and 8.

Unlike the individual tube designs of FIGS. 14-16, FIGS. 17-19 illustrate catheter alternatives constructed of multi-lumen extrusions. As shown in FIG. 17, a catheter 214 with a non-circular lumen 216 and a circular lumen 218 may be used. FIG. 18 shows a version of a catheter 220 with multiple non-circular gas lumens 222 and a single circular liquid lumen 224. A variation of FIG. 18 is the catheter 226 of FIG. 19, where multiple non-circular gas lumens 228 are positioned adjacent circular (or non-circular) liquid lumens 230. The arrangement of FIG. 19 can allow for a binary solution to be delivered through the liquid lumens, so that separate components are delivered through each liquid lumen.

The multiple liquid lumen or tube configurations for the catheter can be used in simultaneous or consecutive delivery plans. For example, in one application, a catheter with multiple liquid lumens can be used so that a first substance is delivered to one region in the body and the catheter is then manipulated so that the catheter can next deliver a different substance to a second region in the body without the need to use separate catheters. Alternatively, the multi liquid lumen catheter can also be used for consecutive delivery of substances to the same region in the body. As an example, a physician may wish to clean the region before applying a treatment. In this instance, a cleaning substance, such as a saline solution, may be delivered through a first lumen to wash the target region and a second substance may be delivered through a second liquid lumen to apply the desired treatment. As mentioned previously, the multiple lumens can be used to simultaneously deliver substances, e.g. binary solutions, so that the mixture is aerosolized and delivered at desired times and in the desired amount. Alternatively, one of the lumens may be used to remove a substance from the body cavity by application of a negative pressure at the proximal end of the catheter.

Figure 20:
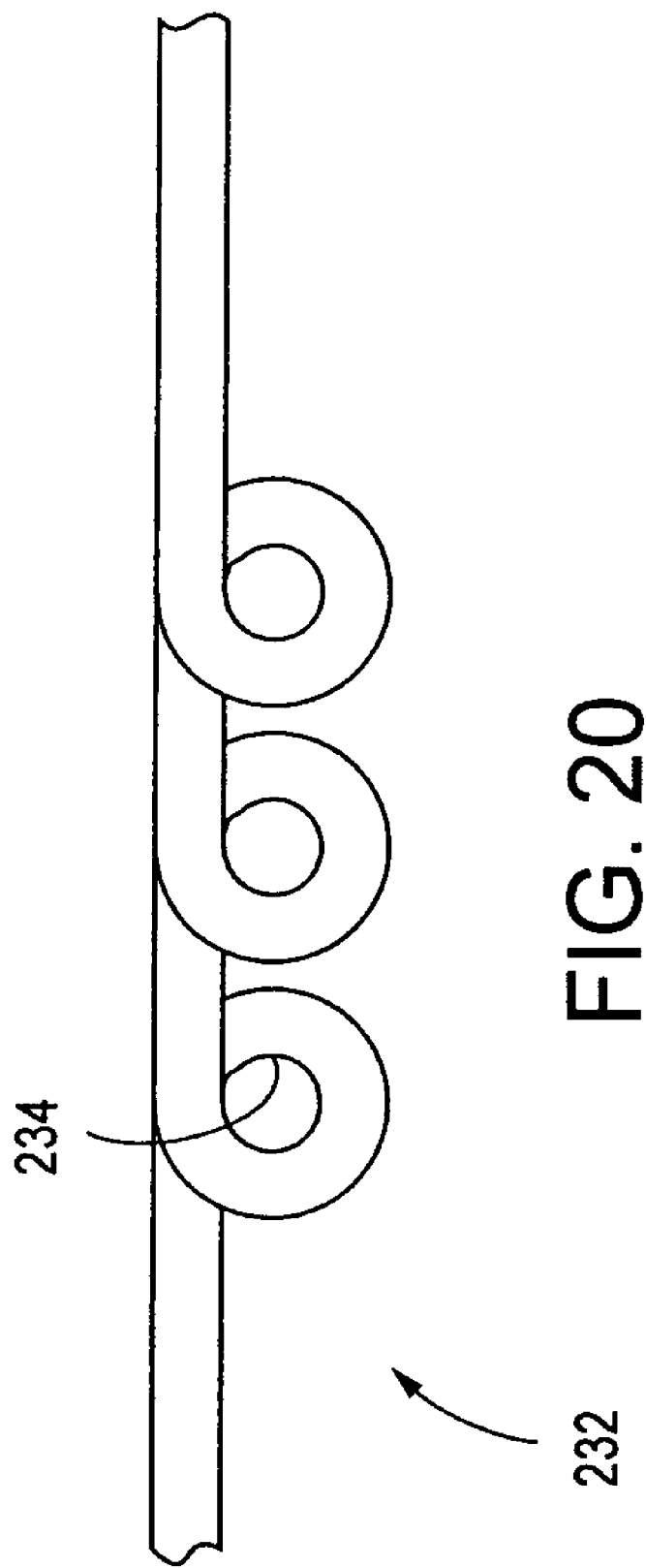
FIG. 20 is a sectional view of a catheter showing a spiral or helically pre-shaped end.
Figure 26:
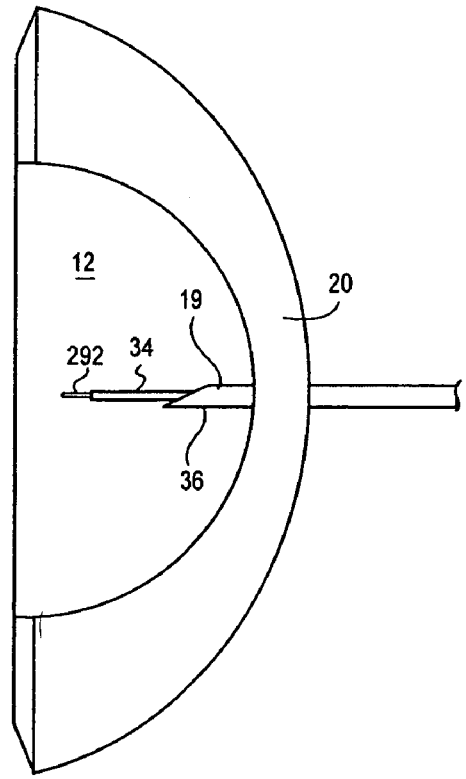
FIG. 26 illustrates an alternative catheter having a pre-shaped straight distal portion.

The pre-shaped catheter may be straight, flexibly jointed or curved. A version of a pre-shaped catheter with a straight shape 292 is shown in FIG. 26. One alternative configuration of a curved version is illustrated in FIG. 20. In FIG. 20, the distal end of a catheter 232 is shown with a helical end 234. The helix may have a single turn or a plurality of turns. An application of a helical-ended catheter is that the action of inserting the end of the catheter into a body cavity or body lumen will result in a circular/helical distribution of a substance as the catheter tip emerges. While many different dimensions for the various catheter embodiments described above are contemplated, in one embodiment the outer diameter may be in the range of 0.5 mm to 200 mm. One preferred diameter for the catheter embodiment seen of FIG. 1 is approximately 1 mm. The introducer used with a particular catheter would then be sized appropriately for that particular catheter. The catheter shaft may be constructed of flexible, resilient material, such as polymeric material, or of flexible material with resilient re-enforcing members. Liquid lumen (s) of the catheter may be pre-filled during the manufacturing process or supplied from reservoir.

Nozzles on the catheters may be tapered or untapered. In some cases, it may be desirable to select a nozzle configuration, gas and/or liquid supply pressure and flow to produce a particle size and inertia to maximize local impaction. In other cases it may be desirable to minimize local impaction and instead create a "fogging" effect.

Figure 21:
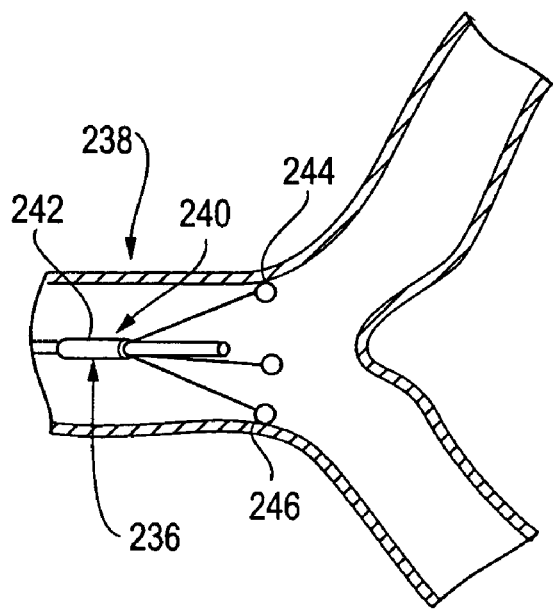
FIG. 21 is a sectional view of an embodiment having a catheter position limiter attached to a catheter.
Figure 22:
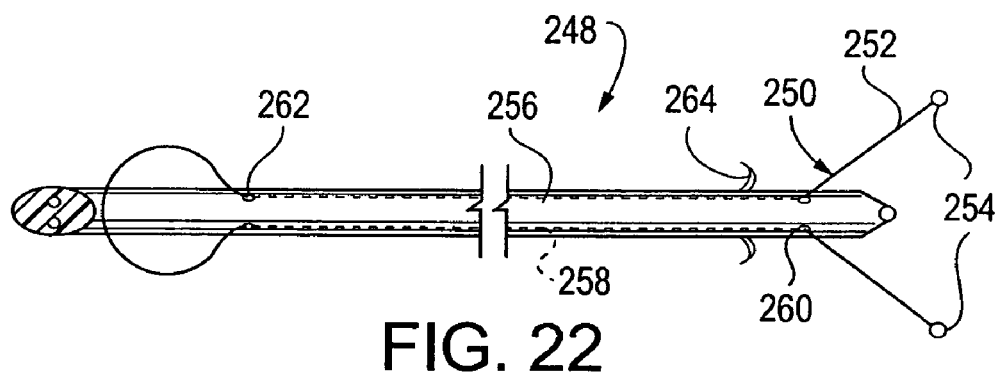
FIG. 22 is a sectional view of an alternative embodiment of the catheter position limiter of FIG. 21.
Figure 23:
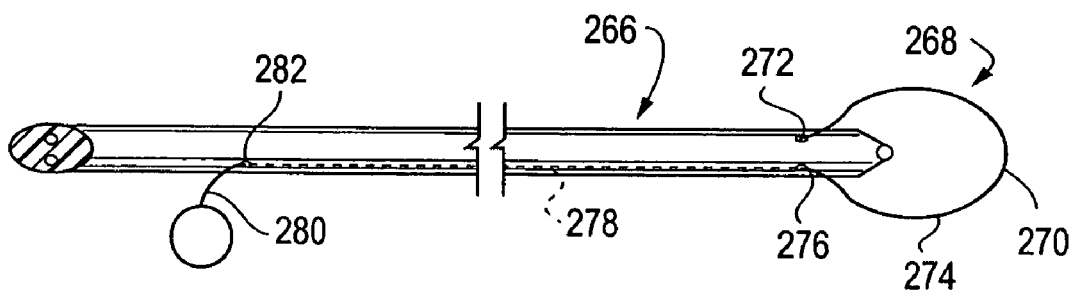
FIG. 23 is a sectional view of a second alternative embodiment of the catheter position limiter of FIG. 21.

In other embodiments, as shown in FIGS. 21-23, a position limiting mechanism may be incorporated on the catheter. Examples of catheter positioning mechanisms may also be found in U.S. Pat. No. 6,729,334, the entirety of which is incorporated herein by reference. The embodiment of FIG. 21 shows a nebulization catheter 236 extending into a body lumen 238. The nebulization catheter 236 may be similar to any of the catheter embodiments described above. Located around a distal portion of the nebulization catheter 236 is a spring position limiter 240. The spring position limiter 240 includes a retainer ring 242 fixed to the shaft of the nebulization catheter 236 and a plurality of arms 244 connected to the ring 242. In one embodiment, there are three arms 244. The arms are flexible and resilient. The arms may be made of a spring tempered metal or a suitable plastic. Located at the end of each of the arms 244 opposite its connection to the ring 242 is a ball 246. The spring position limiter 240 helps prevent the end of the catheter from contacting any tissue. When it is necessary to remove the nebulizing catheter 236, it can be withdrawn in a proximal direction back into the insertion device. In one embodiment, the arms are formed of a thin resilient wire or polymer, preferably less than approximately 0.015 inches in diameter. The arms and/or the balls may be made of, or coated with, a radiopaque material.

FIG. 22 shows an alternative embodiment of the nebulization catheter. A nebulization catheter 248 includes a position limiter device 250. The limiter device 250 includes a plurality of arms 252 that are formed to resiliently extend outward from the axis of the catheter shaft to engage a cavity or body lumen wall depending upon the desired location of the distal end of the nebulization catheter. At the ends of each of the arms 252 are balls 254. The proximal ends of the arms 252 are formed of wires 256 that extend through lumens 258 in the shaft of the catheter 248. Each of the lumens 258 has a distal opening 260 from which an arm can extend. The distal openings are approximately 0.10-1 cm from the distal end of the catheter shaft. The proximal ends of the wires 256 exit the lumens 258 of the nebulization catheter via openings 262 that are close to the proximal end of the catheter in a portion of the catheter that would normally be outside the patient's body during use. Thus, the proximal ends of the wires 256 are accessible to the physician during use. By pulling and pushing on the proximal ends of the wires 256, the portion of the arms 252 that extend from the openings 260 can be adjusted. Thus, the arms 252 can be adjusted from a fully retracted to a fully advanced position by pulling or pushing on the proximal ends of the wires 256. In addition, since the proximal ends can of the wires 256 be adjusted in any intermediate position between the fully retracted and fully advanced positions, the physician can adjust the size of the position limiting device to keep the catheter at any appropriate minimum distance, as desired. Because the wires 256 should assume a desired shape when advanced out of the lumens in which they are contained during positioning, it is preferable that they be formed of a material that has shape memory properties so that the desired expanded shape can be imparted to the wires during manufacture. In one embodiment, the wires may be formed of nitinol.

In one preferred embodiment, a second position limiting device 264 is also provided. The second position limiting device 264 is located on the shaft of the nebulization catheter 248 proximally from the first limiting device 250. The second position limiting device 264 may be formed of resilient wings formed of a material such as plastic or metal that extend radially outward from the shaft. The second (or proximal) position limiting device 264 helps keep the distal portion of the catheter 248 from contacting tissue surrounding the body cavity or lumen.

FIG. 23 shows another alternative embodiment of the position limiter. A nebulizing catheter 266 is shown. The nebulizing catheter 266 includes a position limiting device 268. The centering device 268 includes a wire loop 270 located at a distal end of the catheter. One end 272 of the loop 270 connects to the distal end of the nebulizing catheter shaft. The other end 274 of the wire loop 270 enters an opening 276 in the shaft that communicates with a lumen 278 that extends to a proximal end of the catheter 266. A proximal end 280 of the wire exits the lumen 266 via an opening 282 in a proximal portion of the nebulizing catheter which is normally outside the patient's body during use. The size of the wire loop 270 can be adjusted by advancing or withdrawing the proximal end 280 of the wire.

Figure 24:
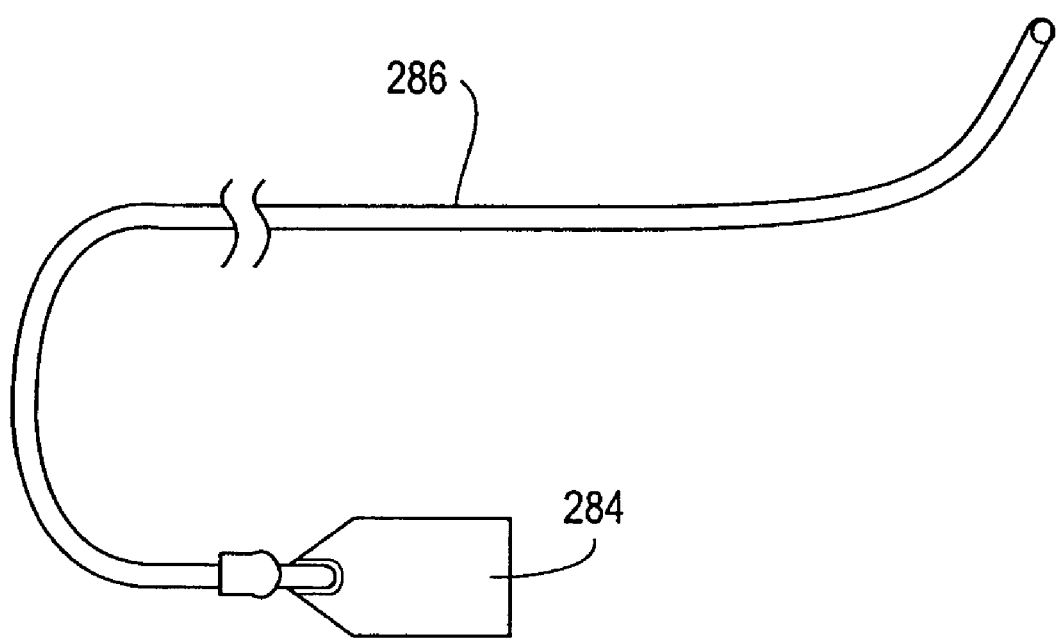
FIG. 24 illustrates a pressurized canister containing a substance or solution under pressure connected to a catheter.

Various types of sources of substances are contemplated for use with the embodiments discussed above. In mulitilumen embodiments, any of a number of known pump systems may be connected to the proximal ends of the catheter to supply dry or liquid substances. One example of an arrangement for supplying doses of a dry substance may be found in U.S. Pat. No. 6,719,960, the entirety of which is incorporated herein by reference. As shown in FIG. 24, in single lumen embodiments a pressurized canister 284 containing a solution or substance may be attached to the proximal end of the catheter 286 for unassisted, or assisted, creation of an aerosolized substance that can be delivered. Other arrangements of canisters, including without limitation those incorporated in metered dose inhalers or with built-in metering valves, may be used. An example of this type of canister-catheter arrangement is found in U.S. Pat. No. 6,079,413, the entirety of which is incorporated herein by reference.

In the various embodiments above, the orientation may be determined from graduated markings or other indicia in the proximal portion of the catheter shaft. As discussed above, graduated markings indicating insertion depths of the catheter may be included. In addition, the catheter shaft may be marks to indicate the rotational orientation of the catheter tip. Such markings may be in the form of longitudinally oriented marks along the proximal portion of the catheter shaft. These marks, as with the longitudinal insertion depth marks described above, may be of the same or different colors, at even or uneven spacings, in various textures or geometric shapes, or any of a number of other visual, tactile, electronic or other formats. Additionally, or independently, the distal portion of the catheter, intended to be positioned in the body cavity, may also incorporate materials or markings designed to be visible to ultrasonic, X-ray or other types of imaging equipment. These may include radial-opaque polymer blends, inks, metal markers, or texture services designed to reflect ultrasonic energy. In some embodiments, a fiber optic cable incorporated in or running parallel to the catheter may be used to visualize from outside the body cavity the specific target receiving treatment.

Although an aerosolized substance comprising a medicine has primarily been discussed with respect to the above-embodiments, the system of the present invention may be used to manipulate an instrument or catheter tip to deliver a light or other electromagnetic treatment, or to deliver a directed stream of therapeutic gas, powder, foam, gel or other form of substance. Additionally, while the examples provided above discuss insertion into a body cavity through an abdominal wall, the system may be used for applying substance to any natural or artificially created anatomical cavity, lumen or hollow organ.

Elements of this invention pertaining to remote directional and positional control of an aerosol generation nozzle may also be applied to other probe or catheter-type surgical devices that deliver focused streams of gasses, plasmas, foams, gels, powders, or liquids or energy beams through a directional nozzle, orifice, lumen, lens, aperture or directional generation source in which remote directional control of the output is desirable. It is contemplated that elements of this invention pertaining to the directional of positional control of a stream or cone of material energy may be utilized in multifunction surgical instruments that combine aerosol delivery with other surgical capabilities including, but not limited to, cutting, oblation, cauterization, biopsies, freezing, suturing or closing incisions. It is also contemplated that other devices, aside from an introducer needle may be used to guide a catheter or other tube into a body cavity, for example endoscopes, surgical ports, and so on. These other types of probe or catheter-type devices may utilize other methods of aerosol generation, including, without limitation, vibratory, ultrasonic, pneumatic and electro-hydraulic methods.

As discussed above, a method and apparatus for creating a medicated atmosphere in an organ or body cavity has been disclosed. The method permits a controlled application of a substance, for example via creation of an aerosol cloud, allowing for the deposition of a substance comprising a medicament on all or a selected number of interior surfaces. The system comprises a tube or aerosolization catheter that can be manipulated during use and an introduction device for the introduction and manipulation, rotation and/or longitudinal positioning, of the tube or aerosolization catheter. The method includes inserting the tube or catheter into a body cavity and adjusting an angle or orientation of the exit end of the tube or catheter so that a substance provided to the tube or catheter will be controllably applied to the body cavity.

It is intended that the foregoing detailed description be regarded as illustrative rather than limiting, and that it be understood that the following claims, including all equivalents, are intended to define the scope of this invention.

We claim:

1. A system for manipulating a catheter used for delivering a substance to a body cavity of a patient, the system comprising:
   a catheter comprising at least one lumen or tube, the catheter having a proximal end configured for receiving a substance intended for delivery to a body cavity and a distal end comprising a flexible tip biased in a pre-shaped curve; and
   an introducer apparatus comprising:
      a body defining a bore sized to receive the catheter;
      a catheter adjustment mechanism having a rotatable knob that is rotatably attached to the body and offset from the catheter, the catheter adjustment mechanism configured to rotate the catheter relative to the body of the introducer apparatus about a longitudinal axis of the catheter via rotation of the rotatable knob, wherein the catheter is axially movable relative to the rotatable knob;

wherein the catheter adjustment mechanism is operably connected to the catheter to simultaneously control both axial and rotational orientation of the catheter relative to the body of the introducer apparatus; and wherein the catheter adjustment mechanism further comprises:
- a first gear arrangement operably connected with the rotatable knob and configured to rotate the catheter relative to the body in response to rotation of the rotatable knob; and
- a second gear arrangement operably connected with the rotatable knob and configured to move the catheter longitudinally relative to the body in response to rotation of the rotatable knob simultaneously with rotation of the catheter.

2. The system of claim 1, wherein the catheter comprises a plurality of tubes.

3. The system of claim 1, wherein the catheter comprises a plurality of lumens.

4. The system of claim 1, wherein the catheter comprises a position limiter positioned to prevent contact of a distal end of the catheter with a wall of a body cavity.

5. The system of claim 1, wherein the catheter adjustment mechanism further comprises a rotational position indicator, operatively connected with the rotatable knob and configured to identify a rotational position of the flexible tip.

6. The system of claim 5, wherein the catheter adjustment mechanism further comprises a longitudinal position indicator configured to identify a longitudinal position of the catheter.

7. A system for manipulating a catheter used for delivering a substance to a body cavity of a patient, the system comprising:
- a catheter comprising at least one lumen or tube, the catheter having a proximal end configured for receiving a substance intended for delivery to a body cavity and a distal end comprising a flexible tip biased in a preshaped orientation; and
- an introducer apparatus comprising:
- a body defining a bore sized to receive the catheter; and
- means for simultaneously rotating the catheter relative to a body of the introducer apparatus and changing an angle of deflection of the flexible tip exclusively via rotation of a knob rotatable relative to the body of the introducer apparatus.

8. The system of claim 7, further comprising a needle releasably connected with the introducer apparatus.

9. The system of claim 7, further comprising a blunt-ended single lumen releasably connected with the introducer apparatus.

\* \* \* \* \*